United States Patent
Walter et al.

(10) Patent No.: US 7,160,901 B2
(45) Date of Patent: *Jan. 9, 2007

(54) SUBSTITUTED INDOLINONES, PREPARATION THEREOF AND THEIR USE AS PHARMACEUTICAL COMPOSITIONS

(75) Inventors: Rainer Walter, Biberach (DE); Armin Heckel, Biberach (DE); Gerald Roth, Biberach (DE); Joerg Kley, Mittelbiberach (DE); Gisela Schnapp, Biberach (DE); Martin Lenter, Ulm (DE); Jacobus Van Meel, Moedling (AT); Walter Spevak, Oberronhrbach (AT); Ulrike Weyer-Czernilofsky, Baden (AT)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 234 days.

This patent is subject to a terminal disclaimer.

(21) Appl. No.: 10/646,423

(22) Filed: Aug. 22, 2003

(65) Prior Publication Data

US 2004/0044222 A1    Mar. 4, 2004

Related U.S. Application Data

(62) Division of application No. 10/002,939, filed on Nov. 1, 2001, now Pat. No. 6,638,965.

(60) Provisional application No. 60/251,055, filed on Dec. 1, 2000.

(30) Foreign Application Priority Data

Nov. 1, 2000   (DE)   ................... 100 54 019

(51) Int. Cl.
   *A61K 31/454*   (2006.01)
   *C07D 401/10*   (2006.01)
(52) U.S. Cl. ...................... 514/323; 546/201

(58) Field of Classification Search ................ 546/201; 514/323

See application file for complete search history.

(56) References Cited

U.S. PATENT DOCUMENTS

| 6,794,395 B1* | 9/2004 | Roth et al. ................ 514/323 |
| 2004/0044053 A1* | 3/2004 | Walter et al. ............. 514/365 |
| 2004/0204458 A1* | 10/2004 | Roth et al. ................ 514/323 |

FOREIGN PATENT DOCUMENTS

| DE | 100 29 285 | 12/2001 |
| EP | 1 070 705 A1 | 1/2001 |
| WO | WO 99 10325 | 3/1999 |
| WO | WO 99 15500 | 4/1999 |
| WO | WO 99 51574 | 10/1999 |
| WO | WO 00 55159 | 9/2000 |
| WO | WO 01 16130 | 3/2001 |
| WO | WO 01 27081 | 4/2001 |

* cited by examiner

*Primary Examiner*—Joseph K. McKane
*Assistant Examiner*—Rebecca Anderson
(74) *Attorney, Agent, or Firm*—Michael P. Morris; Mary-Ellen M. Devlin; Alan R. Stempel

(57) ABSTRACT

Indolinones of general formula I

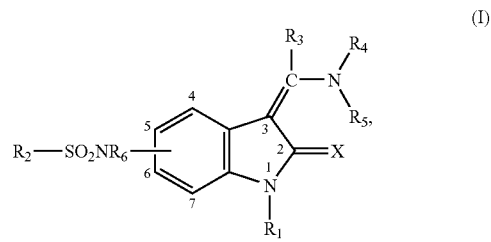

which are inhibitors of cell proliferation, particularly of tumor cells, and inhibitors of protein kinases.

13 Claims, No Drawings

SUBSTITUTED INDOLINONES, PREPARATION THEREOF AND THEIR USE AS PHARMACEUTICAL COMPOSITIONS

RELATED APPLICATIONS

This is a division of Ser. No. 10/002,939 filed Nov. 1, 2001 now U.S. Pat. No. 6,638,965. Benefit of U.S. Provisional Application Ser. No. 60/251,055, filed on Dec. 1, 2000 is hereby claimed.

DESCRIPTION OF THE INVENTION

The present invention relates to new substituted indolinones of general formula

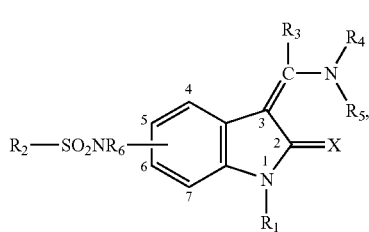

(I)

the isomers, the salts thereof, particularly the physiologically acceptable salts thereof which have valuable properties.

The above compounds of general formula I wherein $R_1$ is a hydrogen atom or a prodrug group have valuable pharmacological properties, particularly an inhibiting effect on the proliferation of cultivated human tumour cells, but also on the proliferation of other cells, particularly endothelial cells, e.g. in angiogenesis, on various kinases, particularly on receptor tyrosine kinases (such as, for example, VEGFR2, EGFR, IGF1R ), non-receptor tyrosine kinases (such as e.g. c-src), and serine/threonine kinases (such as e.g. cyclin-dependent kinases), and the other compounds of the above general formula I wherein $R_1$ does not denote a hydrogen atom or a prodrug group, are valuable intermediate products for the preparation of the compounds mentioned above.

The present invention thus relates to the above compounds of general formula I, wherein X denotes an oxygen or sulphur atom, $R_1$ denotes a hydrogen atom, a $C_{1-4}$-alkoxycarbonyl or $C_{2-4}$-alkanoyl group, $R_2$ denotes a $C_{1-6}$-alkyl group optionally substituted by one or more halogen atoms or a phenyl group or a $C_{2-6}$-alkenyl group optionally substituted by a phenyl group, wherein the phenyl moiety may be substituted in each case by a fluorine, chlorine, bromine or iodine atom, by a $C_{1-3}$-alkyl or $C_{1-3}$-alkoxy group, a phenyl group which may be mono- or disubstituted by fluorine, chlorine, bromine or iodine atoms, by $C_{1-3}$-alkyl or $C_{1-3}$-alkoxy groups, wherein the substituents may be identical or different, a phenyl group substituted by a trifluoromethyl, carboxy, $C_{1-3}$-alkoxycarbonyl, aminocarbonyl, cyano, aminomethyl, nitro or amino group, a $C_{4-6}$-alkyl, $C_{3-7}$-cycloalkyl, trimethylphenyl or naphthyl group, a 5-membered heteroaromatic group optionally substituted by a $C_{1-3}$-alkyl group, which contains, in the heteroaromatic moiety, an imino group optionally substituted by a $C_{1-3}$-alkyl group, an oxygen or sulphur atom, an imino group optionally substituted by a $C_{1-3}$-alkyl group and an oxygen, sulphur or nitrogen atom, an imino group optionally substituted by a $C_{1-3}$-alkyl group and two nitrogen atoms, or an oxygen or sulphur atom and two nitrogen atoms, and to which a phenyl ring may be fused via two adjacent carbon atoms, or denotes a 6-membered heteroaromatic group optionally substituted by a $C_{1-3}$-alkyl group, which contains one or two heteroatoms in the heteroaromatic moiety and to which a phenyl ring may be fused via two adjacent carbon atoms, $R_3$ denotes a hydrogen atom or a $C_{1-6}$-alkyl group, a phenyl group optionally substituted by a fluorine, chlorine or bromine atom, by a $C_{1-3}$-alkyl, hydroxy, $C_{1-3}$-alkoxy, $C_{1-3}$-alkylsulphenyl, $C_{1-3}$-alkylsulphinyl, $C_{1-3}$-alkylsulphonyl, phenylsulphenyl, phenylsulphinyl, phenylsulphonyl, nitro, amino, $C_{1-3}$-alkylamino, di-($C_{1-3}$-alkyl)-amino, $C_{2-5}$-alkanoylamino or N—($C_{1-3}$-alkylamino)-$C_{2-5}$-alkanoylamino group, R4 denotes a phenyl or naphthyl group optionally substituted by $R_7$, which may additionally be substituted by a chlorine or bromine atom or a nitro group, a 5-membered heteroaromatic group which contains an imino group, an oxygen or sulphur atom or an imino group, an oxygen or sulphur atom and one or two nitrogen atoms, or a 6-membered heteroaromatic group which contains one, two or three nitrogen atoms, while the abovementioned 5- and 6-membered heteroaromatic groups may additionally be substituted by a chlorine or bromine atom or by a methyl group or wherein a phenyl ring may be fused to the abovementioned 5- and 6-membered heteroaromatic groups via 2 adjacent carbon atoms, or $R_5$ and $R_6$ in each case independently of one another denote hydrogen atoms or $C_{1-3}$-alkyl groups, and $R_7$ denotes a fluorine, chlorine, bromine or iodine atom or a cyano group, a methoxy group or a $C_{2-3}$-alkoxy group, which may be substituted in the 2 or 3 position by an amino, $C_{1-3}$-alkylamino, di-($C_{1-3}$-alkyl)-amino or 5- to 7-membered cycloalkyleneimino group, while in each case an alkyl moiety in the abovementioned alkylamino and dialkylamino groups may additionally be substituted by a phenyl group, a trifluoromethyl, nitro, amino, $C_{1-3}$-alkylamino, di-($C_{1-3}$-alkyl)-amino, $C_{2-5}$-alkanoylamino, N—($C_{1-3}$-alkyl)-$C_{2-5}$-alkanoylamino, $C_{1-5}$-alkylsulphonylamino, N—($C_{1-3}$-alkyl)-$C_{1-5}$-alkylsulphonylamino, phenylsulphonylamino, N—($C_{1-3}$-alkyl)-phenylsulphonylamino, aminosulphonyl, $C_{1-3}$-alkylaminosulphonyl or di-($C_{1-3}$-alkyl)-aminosulphonyl group, while in each case an alkyl moiety in the abovementioned alkylamino and dialkylamino groups may additionally be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, 2-dimethylaminoethylaminocarbonyl or N-methyl-(2-dimethylaminoethyl)-aminocarbonyl group and in each case the alkyl moiety of the abovementioned alkanoylamino or alkysulphonylamino groups may additionally be substituted by a phenyl, amino, $C_{1-3}$-alkylamino, di-($C_{1-3}$-alkyl)-amino or a 4- to 7-membered cycloalkyleneimino group, a $C_{2-4}$-alkylamino group which is terminally substituted in the 2, 3- or 4 position by an amino, $C_{1-3}$-alkylamino, di-($C_{1-3}$-alkyl)-amino, benzylamino, N—($C_{1-3}$-alkyl)-benzylamino, $C_{2-5}$-alkanoylamino or N—($C_{1-3}$-alkyl)-$C_{2-5}$-alkanoylamino group and wherein additionally the amino-hydrogen atom may be replaced by a $C_{2-5}$-alkanoyl, benzoyl, $C_{1-5}$-alkylsulphonyl- or phenylsulphonyl group, while the last-mentioned $C_{2-5}$-alkanoyl or $C_{1-5}$-alkylsulphonyl groups in the alkyl moiety may be substituted by a phenyl group, a carbonyl group which is substituted by a hydroxy, $C_{1-3}$-alkoxy, amino, $C_{1-3}$-alkylamino, N—($C_{1-5}$-alkyl)-$C_{1-3}$-alkylamino or $C_{5-7}$-cycloalkyleneimino group;

a $C_{1-3}$-alkyl group which may be substituted by an amino, $C_{1-5}$-alkylamino, $C_{5-7}$-cycloalkylamino or phenyl-$C_{1-3}$-alkylamino group which may additionally be substituted at the amino nitrogen atom in each case by a $C_{1-4}$-alkyl, $C_{5-7}$-cycloalkyl or $C_{2-4}$-alkenyl- or $C_{1-4}$-alkyl group, while the abovementioned $C_{1-4}$-alkyl substituent in each case may additionally be mono-, di- or trisubstituted by a cyano, carboxy, $C_{1-3}$-alkoxycarbonyl, $C_{2-4}$-alkanoyl, pyridyl, imidazolyl, benzo[1,3]dioxol or phenyl group, while the phenyl group may be substituted by fluorine, chlorine or bromine atoms, by methyl, methoxy, trifluoromethyl, cyano or nitro groups and the substituents may be identical or different, or in the 2, 3 or 4 position by a hydroxy group, a $C_{1-3}$-alkyl group which is substituted by a hydroxy, carboxy, morpholino, thiomorpholino, 1-oxo-thiomorpholino, 1,1-dioxo-thiomorpholino, piperazino, N—($C_{1-3}$-alkyl)-piperazino or N-benzyl-piperazino group, by a 5- to 7-membered cycloalkenyleneimino group or by a 4- to 7-membered cycloalkyleneimino group, while the abovementioned 5- to 7-membered cycloalkyleneimino groups may be substituted by one or two $C_{1-3}$-alkyl groups, which may in turn be terminally substituted by a hydroxy, amino or $C_{2-4}$-alkanoylamino group, or by a $C_{5-7}$-cycloalkyl or phenyl group and by a hydroxy group and in the abovementioned cycloalkyleneimino groups a methylene group adjacent to the nitrogen atom may be replaced by a carbonyl group, a $C_{1-3}$-alkyl group which is substituted by a 5- to 7-membered cycloalkyleneimino group, while a phenyl group optionally mono- or disubstituted by fluorine, chlorine or bromine atoms or by methyl or methoxy groups, wherein the substituents may be identical or different, or an oxazolo, imidazolo, thiazolo, pyridino, pyrazino or pyrimidino group optionally substituted by a fluorine, chlorine, bromine or iodine atom, by a methyl, methoxy or amino group is fused to the abovementioned 5- to 7-membered cycloalkyleneimino groups via 2 adjacent carbon atoms, while the abovementioned monosubstituted phenyl groups may additionally be substituted by a fluorine, chlorine or bromine atom, by a methyl, methoxy or nitro group, or denotes an imidazolyl or 1H—$C_{1-3}$-alkylimidazolyl group.

If $R_1$ denotes a hydrogen atom, the present invention also relates to the tautomeric compounds of formula I'

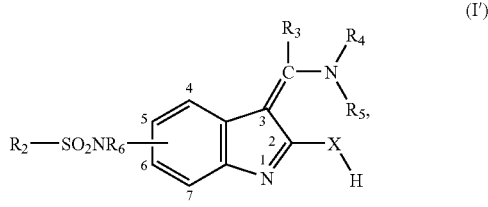

(I')

The invention also relates to compounds of formula I, wherein $R_1$ denotes a cleavable prodrug group.

The invention further relates to pharmaceutical compositions containing the pharmacologically active compound, their use and processes for preparing them.

Preferred compounds of formula I are those wherein the sulphonylamino group of formula $R_2$—$SO_2NR_6$— is linked to the 5-position of the indolinone group.

Preferred compounds of formula I are those wherein
$R_7$ denotes a $C_{1-3}$-alkyl group which is substituted by a hydroxy, carboxy, morpholino, thiomorpholino, 1-oxo-thiomorpholino, 1,1-dioxo-thiomorpholino, piperazino, N—($C_{1-3}$-alkyl)-piperazino or N-benzyl-piperazino group, by a 5- to 7-membered cycloalkenyleneimino group or by a 4- to 7-membered cycloalkyleneimino group, while the abovementioned 5- to 7-membered cycloalkyleneimino groups may be substituted by one or two $C_{1-3}$-alkyl groups, which may in turn be terminally substituted by an amino or $C_{2-4}$-alkanoylamino group, or by a $C_{5-7}$-cycloalkyl or phenyl group and by a hydroxy group and in the abovementioned cycloalkyleneimino groups a methylene group adjacent to the nitrogen atom may be replaced by a carbonyl group.

Also preferred are compounds of formula I wherein
$R_3$ denotes a phenyl group optionally substituted by a fluorine, chlorine or bromine atom, by a $C_{1-3}$-alkyl, hydroxy, $C_{1-3}$-alkoxy, $C_{1-3}$-alkylsulphenyl, $C_{1-3}$-alkylsulphinyl, $C_{1-3}$-alkylsulphonyl, phenylsulphenyl, phenylsulphinyl, phenylsulphonyl, nitro, amino, $C_{1-3}$-alkylamino, di-($C_{1-3}$-alkyl)-amino, $C_{2-5}$-alkanoylamino or N—($C_{1-3}$-alkylamino)-$C_{2-5}$-alkanoylamino group, more particularly a phenyl group optionally substituted by an fluorine, chlorine, bromine or iodine atom, by a $C_{1-3}$-alkyl, $C_{1-3}$-alkoxy, nitro or amino group.

In another preferred embodiment $R_2$ denotes a $C_{1-4}$-alkyl group optionally substituted by one or more halogen atoms or a phenyl group, a $C_{3-5}$-cycloalkyl group or a $C_{2-4}$-alkenyl group optionally substituted by a phenyl group, wherein the phenyl moiety in each case may be substituted by a fluorine, chlorine, bromine or iodine atom or by a $C_{1-3}$-alkyl or $C_{1-3}$-alkoxy.

Moreover, the carboxy, amino or imino groups present in a compound of the above general formula I may be substituted by groups which can be cleaved in vivo.

In addition to the alkoxycarbonyl and alkanoyl groups already mentioned hereinbefore, groups which can be cleaved in vivo may also be included, such as an acyl group such as the benzoyl, pyridinoyl, pentanoyl or hexanoyl group, an allyloxycarbonyl group, a $C_{1-16}$-alkoxycarbonyl group such as the tert.-butyloxycarbonyl, pentyloxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_cCO$—O—($R_d$-$CR_e$)—O—CO-group, wherein $R_c$ denotes a $C_{1-8}$-alkyl, $C_{5-7}$-cycloalkyl, phenyl- or phenyl-$C_{1-3}$-alkyl group, $R_e$ denotes a hydrogen atom, a $C_{1-3}$-alkyl, $C_{5-7}$-cycloalkyl or phenyl group and $R_d$ denotes a hydrogen atom or a $C_{1-3}$-alkyl group or a $R_fCO$—O—($R_gCR_h$)—O-Rest wherein $R_f$ denotes a $C_{1-8}$-alkyl, $C_{5-7}$-cycloalkyl, phenyl or phenyl-$C_{1-3}$-alkyl group, $R_g$ denotes a hydrogen atom, a $C_{1-3}$-alkyl, $C_{5-7}$-cycloalkyl or phenyl group and $R_h$ denotes a hydrogen atom or a $C_{1-3}$-alkyl group, while the abovementioned ester groups may also be used as a group which can be converted in vivo into a carboxy group.

Preferred compounds of the above general formula I are those wherein

X denotes an oxygen atom, $R_1$ denotes a hydrogen atom, $R_2$ denotes a $C_{1-3}$-alkyl group optionally substituted by one or more fluorine atoms or a phenyl group or a $C_{2-4}$-alkenyl group optionally substituted by a phenyl group;

a phenyl group which may be mono- or disubstituted by fluorine, chlorine, bromine or iodine atoms, by $C_{1-3}$-alkyl or $C_{1-3}$-alkoxy groups, wherein the substituents may be identical or different, a phenyl group substituted by a trifluoromethyl, carboxy, $C_{1-3}$-alkoxycarbonyl, aminocarbonyl, cyano, aminomethyl, nitro or amino group, a $C_{4-6}$-alkyl, $C_{3-7}$-cycloalkyl, trimethylphenyl or naphthyl group, or a pyridinyl, quinolyl, isoquinolyl, oxazolyl, isoxazolyl, imidazolyl or 1-($C_{1-3}$-alkyl)-imidazolyl group optionally substituted by a $C_{1-3}$-alkyl group, $R_3$ denotes a hydrogen atom or a $C_{1-4}$-alkyl group, or a phenyl group optionally substituted by a fluorine, chlorine, bromine or iodine atom, by a $C_{1-3}$-alkyl, $C_{1-3}$-alkoxy, nitro or amino group, $R_4$ denotes a phenyl group optionally substituted by $R_7$, which may additionally be substituted by a chloro or nitro group, $R_5$ and $R_6$ in each case denote a hydrogen atom, and $R_7$ denotes a fluorine, chlorine, bromine or iodine atom, a methoxy, nitro, cyano, carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylaminocarbonyl, N-(phenyl-$C_{1-3}$-alkyl)-$C_{1-3}$-alkylaminocarbonyl or 5- to 7-membered cycloalkyleneiminocarbonyl group, a $C_{1-3}$-alkyl group which is substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylaminocarbonyl, N-(phenyl-$C_{1-3}$-alkyl)-$C_{1-3}$-alkylaminocarbonyl, 5- to 7-membered cycloalkyleneiminocarbonyl, amino, $C_{1-3}$-alkylamino, di-($C_{1-3}$-alkyl)-amino, phenyl-$C_{1-3}$-alkylamino, N-(phenyl-$C_{1-3}$-alkyl)-$C_{1-3}$-alkylamino or 5- to 7-membered cycloalkyleneimino group, while the abovementioned 5- to 7-membered cycloalkyleneimino group may be substituted by one or two $C_{1-3}$-alkyl groups, which may in turn be terminally substituted by a hydroxy, amino or $C_{2-4}$-alkanoylamino group, and at the same time in the abovementioned 5- to 7-membered cycloalkyleneimino moieties a methylene group in the 2 position may be replaced by a carbonyl group or in the abovementioned 6- and 7-membered cycloalkyleneimino moieties a methylene group in the 4 position may be replaced by an oxygen atom, by an imino, N—($C_{1-3}$-alkyl)-imino, N-(phenyl-$C_{1-3}$-alkyl)-imino or N—($C_{1-5}$-alkoxycarbonyl)-imino group, an amino, $C_{1-3}$-alkylamino, phenyl-$C_{1-3}$-alkylamino, $C_{1-5}$-alkanoylamino, phenyl-$C_{1-4}$-alkanoylamino, $C_{1-5}$-alkoxycarbonylamino, phenyl-$C_{1-3}$-alkoxycarbonylamino, $C_{1-5}$-alkylsulphonylamino, phenyl-$C_{1-3}$-alkylsulphonylamino- or phenylsulphonylamino group, wherein the hydrogen atom of the amino group may be replaced by a $C_{1-3}$-alkyl group, while the $C_{1-3}$-alkyl moiety may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylaminocarbonyl, N-(phenyl-$C_{1-3}$-alkyl)-$C_{1-3}$-alkylaminocarbonyl, 2-dimethylaminoethylaminocarbonyl, N-methyl-(2-dimethylaminoethyl)-aminocarbonyl- or $C_{4-6}$-cycoalkylenimnocarbonyl group or from position 2 by an amino, $C_{1-3}$-alkylamino, di-($C_{1-3}$-alkyl)-amino, phenyl-$C_{1-3}$-alkylamino, N-(phenyl-$C_{1-3}$-alkyl)-$C_{1-3}$-alkylamino, $C_{2-5}$-alkanoylamino, N—($C_{1-3}$-alkyl)-$C_{2-5}$-alkanoylamino, $C_{1-5}$-alkoxycarbonylamino- or N—($C_{1-5}$-alkoxycarbonyl)-$C_{1-3}$-alkylamino group, imidazolyl or 1-$C_{1-3}$-alkylimidazolyl group.

Particularly preferred compounds of formula I are those wherein $R_7$ denotes a $C_{1-3}$-alkyl group which is substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylaminocarbonyl, N-(phenyl-$C_{1-3}$-alkyl)-$C_{1-3}$-alkylaminocarbonyl, 5- to 7-membered cycloalkyleneiminocarbonyl, amino, $C_{1-3}$-alkylamino, di-($C_{1-3}$-alkyl)-amino, phenyl-$C_{1-3}$-alkylamino, N-(phenyl-$C_{1-3}$-alkyl)-$C_{1-3}$-alkylamino- or 5- to 7-membered cycloalkyleneimino group, while the abovementioned 5- to 7-membered cycloalkyleneimino group may be substituted by one or two $C_{1-3}$-alkyl groups, which may in turn be terminally substituted by an amino or $C_{2-4}$-alkanoylamino group, and at the same time in the above-mentioned 5-to 7-membered cycloalkyleneimino moieties a methylene group may be replaced in the 2 position by a carbonyl group or in the abovementioned 6- and 7-membered cycloalkyleneimino moieties a methylene group in the 4 position may be replaced by an oxygen atom, by an imino, N—($C_{1-3}$-alkyl)-imino, N-(phenyl-$C_{1-3}$-alkyl)-imino or N—($C_{1-5}$-alkoxycarbonyl)-imino group.

Particularly preferred compounds of general formula I are those wherein

X denotes an oxygen atom, $R_1$ denotes a hydrogen atom, $R_2$ denotes a $C_{1-3}$-alkyl group optionally substituted by a phenyl group, a $C_{1-3}$-perfluoroalkyl group or a phenylvinyl group, a phenyl group which may be substituted by a fluorine, chlorine, bromine or iodine atom, by a $C_{1-3}$-alkyl, $C_{1-3}$-alkoxy, nitro, amino, cyano or aminomethyl group, a $C_{4-6}$-alkyl, $C_{3-7}$-cycloalkyl, trimethylphenyl or naphthyl group, a pyridinyl, quinolyl, isoquinolyl, oxazolyl, isoxazolyl, imidazolyl or 1-($C_{1-3}$-alkyl)-imidazolyl group optionally substituted by a $C_{1-3}$-alkyl group, $R_3$ denotes a phenyl group optionally substituted by a fluorine, chlorine, bromine or iodine atom, by a $C_{1-3}$-alkyl, $C_{1-3}$-alkoxy, nitro or amino group, $R_4$ denotes a phenyl group which may be substituted by $R_7$ and additionally by a chlorine atom or a nitro group, while $R_7$ denotes a fluorine, chlorine, bromine or iodine atom, a methoxy, nitro, cyano, carboxy, methoxycarbonyl, aminocarbonyl, methylaminocarbonyl, dimethylaminocarbonyl, benzylaminocarbonyl, N-benzyl-methylaminocarbonyl, pyrrolidinocarbonyl or piperidinocarbonyl group, a methyl or ethyl group which may be substituted by a carboxy, methoxycarbonyl, aminocarbonyl, methylaminocarbonyl, dimethylaminocarbonyl, benzylaminocarbonyl, N-benzyl-methylaminocarbonyl, pyrrolidinocarbonyl, piperidinocarbonyl, amino, $C_{1-4}$-alkylamino, di-$C_{1-4}$-alkylamino, benzylamino, N-benzyl-$C_{1-4}$-alkylamino, $C_{2-4}$-alkanoylamino, N-$C_{1-4}$-alkyl-$C_{2-4}$-alkanoylamino, tert.butyloxycarbonylamino, N-methyl-tert.butyloxycarbonylamino, pyrrolidino, pyrrolidinomethyl, hydroxypyrrolidinomethyl, hydroxymethylpyrrolidinomethyl, piperidino, 4-(3-aminopropyl)-piperidino, 4-(3-acetylaminopropyl)-piperidino, dimethylpiperidino, 2-oxo-piperidino, piperazino, 4-methyl-piperazino, 4-benzyl-piperazino, 4-tert.butoxycarbonyl-piperazino or morpholino group, or an amino, methylamino, ethylamino, $C_{1-3}$-alkanoylamino, phenylacetylamino, tert.butoxycarbonylamino, piperidinomethylcarbonylamino, $C_{1-4}$-alkylsulphonylamino, phenyl-methylsulphonylamino or phenylsulphonylamino group, wherein the hydrogen atom of the amino group may be replaced by a methyl, ethyl or propyl group, while the methyl or ethyl moiety in each case may be substituted by a carboxy, methoxycarbonyl, aminocarbonyl, methylaminocarbonyl, dimethylaminocarbonyl, 2-dimethylaminoethylaminocarbonyl or N-methyl-(2-dimethylaminoethyl)-aminocarbonyl group or the ethyl moiety may also be substituted from position 2 by an amino, methylamino, dimethylamino, benzylalkylamino, N-benzyl-methylamino, $C_{2-3}$-alkanoylamino, N-methyl-$C_{2-3}$-alkanoylamino, tert.butyloxycarbonylamino or N-methyl-tert.butyloxycarbonylamino group, an imidazolyl or 1-methylimidazolyl group, $R_5$ and $R_6$ in each case denote a hydrogen atom, and the isomers and the salts thereof.

Particularly preferred are compounds of formula I wherein $R_4$ denotes a phenyl group substituted by $R_7$ in the 3 or 4 position, particularly in the 4 position.

According to the invention, the new compounds are obtained, for example, by the following methods known in principle from the literature:

a. Reacting a Compound of General Formula

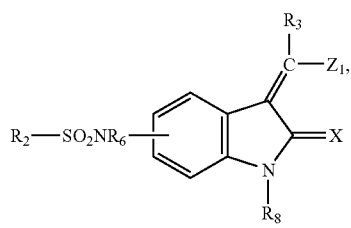

(II)

wherein

X, $R_2$, $R_3$ and $R_6$ are as hereinbefore defined and $R_8$ has one of the meanings given for $R_1$ or may denote a protecting group for the nitrogen atom of the lactam group, while $R_8$ may also represent a bond to a solid phase optionally formed via a spacer, and $Z_1$ denotes a halogen atom, a hydroxy, alkoxy or aralkoxy group, e.g. a chlorine or bromine atom, a methoxy, ethoxy or benzyloxy group, with an amine of general formula

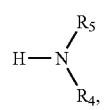

(III)

wherein $R_4$ and $R_5$ are as hereinbefore defined, and if necessary subsequently cleaving any protecting group used for the nitrogen atom of the lactam group or from a solid phase.

The protecting group used for the nitrogen atom of the lactam group may be, for example, an acetyl, benzoyl, ethoxycarbonyl, tert.butyloxycarbonyl or benzyloxycarbonyl group and the solid phase used may be a resin such as a 4-(2',4'-dimethoxyphenylaminomethyl)-phenoxy resin, while the bond may expediently be effected via the amino group, or a p-benzyloxybenzyl alcohol resin, while the bond may expediently be effected via an intermediate member such as a 2,5-dimethoxy-4-hydroxy-benzyl derivative.

The reaction is conveniently carried out in a solvent such as dimethylformamide, toluene, acetonitrile, tetrahydrofuran, dimethylsulphoxide, dichloromethane or mixtures thereof, optionally in the presence of an inert base such as triethylamine, N-ethyl-diisopropylamine or sodium hydrogen carbonate at temperatures between 20 and 175° C., while any protecting group used may simultaneously be cleaved by transamidation.

If $Z_1$ in a compound of general formula II denotes a halogen atom, the reaction is preferably carried out in the presence of an inert base at temperatures between 20 and 120° C.

If $Z_1$ in a compound of general formula II denotes a hydroxy, alkoxy or aralkoxy group, the reaction is preferably carried out at temperatures between 20 and 200° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with an organic base such as ammonia, methylamine, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

Any solid phase used is preferably cleaved using trifluoroacetic acid and water at temperatures between 0 and 35° C., preferably at ambient temperature.

b. Reacting a Compound of General Formula

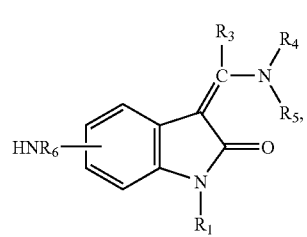

(IV)

wherein $R_1$ and $R_3$ to $R_6$ are as hereinbefore defined, with a compound of general formula $$R_2\text{—}SO_2\text{—}OH \qquad (V),$$

wherein

R₂ is as hereinbefore defined, or with the reactive derivatives thereof.

The reaction is preferably carried out in a solvent such as dichloromethane, diethylether, tetrahydrofuran, toluene, dioxane, acetonitrile, dimethylsulphoxide or dimethylformamide, optionally with a reactive derivative of a compound of general formula V such as the halide thereof, in the presence of an inorganic or tertiary organic base, preferably at temperatures between 0° C. and the boiling temperature of the solvent used, preferably at temperatures between 50 and 100° C.

With a corresponding sulphonic acid the reaction is preferably carried out in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benztriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, expediently at temperatures between 0 and 150° C., preferably at temperatures between 0 and 100° C.

If according to the invention a compound of general formula I is obtained which contains an alkoxycarbonyl group, this can be converted by hydrolysis into a corresponding carboxy compound, or if a compound of general formula I is obtained which contains an amino or alkylamino group, this may be converted by reductive alkylation into a corresponding alkylamino or dialkylamino compound, or if a compound of general formula I is obtained which contains an amino or alkylamino group, this may be converted by acylation into a corresponding acyl compound, or if a compound of general formula I is obtained which contains a carboxy group, this may be converted by esterification or amidation into a corresponding ester or aminocarbonyl compound, or if a compound of general formula I is obtained which contains a nitro group, this can be converted by reduction into a corresponding amino compound, or if a compound of general formula I is obtained which contains a cyano group, this can be converted by reduction into a corresponding aminomethyl compound.

The subsequent hydrolysis is preferably carried out in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

The subsequent reductive alkylation is preferably carried out in a suitable solvent such as methanol, methanol/water, methanol/water/ammonia, ethanol, ether, tetrahydrofuran, dioxane or dimethylformamide, optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, sodium cyanoborohydride, lithium borohydride or lithium aluminium hydride at temperatures between 0 and 100° C., preferably at temperatures between 20 and 80° C.

The subsequent acylation is preferably carried out in a solvent such as methylene chloride, diethylether, tetrahydrofuran, toluene, dioxane, acetonitrile, dimethylsulphoxide or dimethylformamide, optionally in the presence of an inorganic or a tertiary organic base, preferably at temperatures between 20° C. and the boiling temperature of the solvent used. The acylation with a corresponding acid is preferably carried out in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexyl-carbodiimide/N-hydroxysuccinimide, N,N'-dicyclohexylcarbodiimide/1-hydroxy-benztriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylamino-pyridine, N-methyl-morpholine or triethylamine, conveniently at temperatures between 0 and 150° C., preferably at temperatures between 0 and 100° C., and the acylation with a corresponding reactive compound such as an anhydride, ester, imidazolide or halide thereof is optionally carried out in the presence of a tertiary organic base such as triethylamine, N-ethyl-diisopropylamine or N-methyl-morpholine at temperatures between 0 and 150° C., preferably at temperatures between 50 and 100° C.

The subsequent esterification or amidation is expediently carried out by reacting a corresponding reactive carboxylic acid derivative with a corresponding alcohol or amine as described hereinbefore.

The subsequent reduction of a nitro group is preferably carried out by hydrogenolysis, e.g. with hydrogen in the presence of a catalyst such as palladium/charcoal or Raney nickel in a solvent such as methanol, ethanol, ethyl acetate, dimethylformamide, dimethylformamide/acetone or glacial acetic acid, optionally with the addition of an acid such as hydrochloric acid or glacial acetic acid at temperatures of between 0 and 50° C., but preferably at ambient temperature, and at a hydrogen pressure of 1 to 7 bar, but preferably 3 to 5 bar.

The subsequent reduction of a cyano group is preferably carried out by hydrogenolysis, e.g. with hydrogen in the presence of a catalyst such as palladium/charcoal or Raney nickel in a solvent such as methanolic ammonia, ethanolic ammonia, ethyl acetate, dimethylformamide, dimethylformamide/acetone, dichloromethane or glacial acetic acid, optionally with the addition of an acid such as hydrochloric acid or glacial acetic acid at temperatures of between 0 and 50° C., but preferably at ambient temperature, and at a hydrogen pressure of 1 to 7 bar, but preferably 3 to 5 bar.

In the reactions described hereinbefore, any reactive groups present such as carboxy, amino, alkylamino or imino groups may be protected during the reaction by conventional protecting groups which are cleaved again after the reaction.

For example, a protecting group for a carboxyl group may be a trimethylsilyl, methyl, ethyl, tert.butyl, benzyl or tetrahydropyranyl group and protecting groups for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, chiral compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. An optically active alcohol may be for example (+)- or (−)-menthol and an optically active acyl group in amides, for example, may be a (+)- or (−)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid or methanesulphonic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae II to V used as starting materials are known from the literature in some cases or may be obtained by methods known from the literature or are described in the Examples. For example, the compounds of general formula IV are described in German Patent Application 198 24 922.5 of 4 Jun. 1998.

As already mentioned hereinbefore, the new compounds of general formula I wherein $R_1$ denotes a hydrogen atom or a prodrug group have valuable pharmacological properties, particularly an inhibiting effect on the proliferation of cultivated human cells, especially tumour cells, but also on the proliferation of other cells, particularly endothelial cells, e.g. in angiogenesis.

For example, the compounds listed in Table 1 were tested for their biological properties as follows:

Test 1

Inhibition of the Proliferation of Cultivated Human Tumour Cells

Cells of the Leiomyosarcoma tumour cell line SK-UT-1B or non-small-cell lung tumour cell line NCI-H460 (obtained from the American Type Culture Collection (ATCC)) were cultivated in Minimum Essential Medium with non-essential amino acids (Gibco), supplemented with sodium pyruvate (1 mMol), glutamine (2 mMol) and 10% foetal calf serum (Gibco) or RPMI1640 Medium (Gibco) and 10% foetal calf serum (Gibco) and harvested in the logarithmic growth phase. Then the SK-UT-1B cells were placed in Cytostar® multi-well plates (Amersham) at a density of 4000 cells per well or 3000 cells per well for NCI-H460 cells and incubated overnight in an incubator. Various concentrations of the compounds (dissolved in DMSO; final concentration: 0.1%) were added to the cells. After 48 hours' incubation, $^{14}$C-thymidine (Amersham) was added to each well and incubation was continued for a further 24 hours. The quantity of $^{14}$C-thymidine which was incorporated into the tumour cells in the presence of the inhibitor and which represents the number of cells in the S phase was measured in a Wallace 1450 Microbeta Liquid Scintillation Counter. $IC_{50}$ values for the inhibition of the proliferation (=inhibition of incorporated $^{14}$C-thymidine) were calculated, correcting for the background radiation. All the measurements were done twice.

Test 2

In Vivo Effects on Tumour-Bearing Nude Mice $10^6$ cells [SK-UT-1B, or non-small cell lung tumour NCI-H460 (obtained from ATCC)] in a volume of 0.1 ml were injected subcutaneously into male and/or female nude mice (NMRI nu/nu; 25–35 g; N=10–20); alternatively, small fragments of SK-UT-1B or NCI-H460 cell clumps were implanted subcutaneously. One to three weeks after injection or implantation an inhibitor was administered orally (by oesophageal tube) daily for a period of 2 to 4 weeks. The tumour size was measured three times a week using a digital sliding gauge. The effect of a compound on the tumour growth was determined as a percentage inhibition compared with a control group treated with placebo.

The following Table contains the results obtained with the in vitro Test 1 (++ denotes <0.01 μM, + denotes 0.01–1.0 μM):

| Compound (Example No.) | Inhibition of SKUT-1B proliferation |
|---|---|
| 2 | + |
| 4 | ++ |
| 9 | + |
| 12 | + |
| 20 | + |
| 22 | + |
| 23 | + |
| 31 | ++ |
| 36 | ++ |
| 42 | + |
| 56 | ++ |
| 58 | + |
| 66 | ++ |
| 70 | + |
| 71 | + |
| 72 | + |
| 80 | ++ |
| 88 | + |
| 98 | + |
| 99 | ++ |
| 101 | ++ |
| 104 | ++ |
| 112 | ++ |
| 117 | + |
| 120 | ++ |
| 134 | ++ |
| 142 | + |
| 143 | + |
| 144 | + |
| 145 | + |
| 158 | + |
| 164 | + |
| 186 | ++ |
| 207 | + |

In view of their biological properties, the new compounds of general formula I, their isomers and their physiologically acceptable salts are suitable for treating conditions characterised by excessive or anomalous cell proliferation.

Such diseases include (without any claim to completeness): viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy).

The new compounds may be used for the short-term or long-term treatment of the abovementioned conditions, possibly in conjunction with other state-of-the-art compounds such as other cytostatics.

The dosage required to achieve the desired effect is expediently from 0.1 to 30 mg/kg, preferably 0.3 to 10 mg/kg, by intravenous route and 0.1 to 100 mg/kg, preferably 0.3 to 30 mg/kg by oral route, in each case 1 to 4 times a day. For this purpose, the compounds of formula I prepared according to the invention, optionally combined with other active substances, may be formulated with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearylalcohol, carboxymethylcellulose or fatty substances such as hard fat or suitable mixtures thereof, to produce conventional galenic preparations such as plain or coated tablets, capsules, powders, suspensions or suppositories or as solutions for injections or infusions.

The Examples which follow are intended to illustrate the invention without restricting it:

Abbreviations Used:

| | |
|---|---|
| CDI | N,N'-carbonyldiimidazole |
| DMF | dimethylformamide |
| DMSO | dimethylsulphoxide |
| TBTU | O-(benzotriazol-1-yl)-N,N,N'-N'-bis(tetramethylene)-uronium hexafluorophosphate |
| THF | tetrahydrofuran |

Preparation of the Starting Compounds:

EXAMPLE I

4-[N-Acetyl-N-(2-trifluoracetylaminoethyl)-amino]-aniline a. 4-(2-tert.Butoxycarbonylamino-ethylamino)-nitrobenzene 4.2 g (29.7 mmol) of N-tert.butoxycarbonyl-ethylenediamine, 5.0 g (31.2 mmol) of 4-fluoro-nitrobenzene and 7.0 g (50.6 mmol) of potassium carbonate are stirred in 25 ml of DMSO for 9 hours at 60° C. After cooling the mixture is diluted with water and extracted with ethyl acetate. The combined organic extracts are dried and evaporated down. The residue is stirred with petroleum ether, decanted off and evaporated down again. The product is stirred with ether and suction filtered.

Yield: 3.2 g (38% of theory), Melting point: 119° C. $R_f$ value: 0.5 (silica gel; toluene/ethyl acetate=7:3) $C_{13}H_{19}N_3O_4$ (281.31) Mass spectrum: $(M-H)^-=280$ b. 4-(2-trifluoroacetylamino-ethylamino)-nitrobenzene 1.5 g (5.3 mmol) of 4-(2-tert.butoxycarbonylamino-ethylamino)-nitrobenzene are stirred in 15 ml of trifluoroacetic acid for 3 hours at ambient temperature. Then 0.8 ml (5.7 mmol) of trifluoroacetic acid anhydride are added while cooling with ice. The reaction is left overnight to come up to ambient temperature. It is then evaporated down, diluted with water and made alkaline with sodium hydrogen carbonate. The crude product is suction filtered and purified by chromatography (silica gel; dichloromethane/methanol=98:2).

Yield: 1.2 g (81% of theory), $R_f$ value: 0.5 (silica gel; dichloromethane/methanol=19:1) $C_{10}H_{10}F_3N_3O_3$ (277.21) Mass spectrum: $(M-H)^-=276$ c. 4-[N-Acetyl-N-(2-trifluoroacetylamino-ethyl)-amino]-nitrobenzene 0.6 g (2.1 mmol) of 4-(2-trifluoroacetylamino-ethylamino)-nitrobenzene are dissolved in 10 ml of glacial acetic acid and after the addition of 2 ml (21.2 mmol) of acetic acid anhydride stirred for 5 hours at 80° C. and overnight at ambient temperature. The solvent is distilled off, the residue is made alkaline with sodium hydrogen carbonate and extracted with ethyl acetate. The combined organic extracts are dried and evaporated down.

Yield: 0.7 g (97% of theory), $R_f$ value: 0.4 (silica gel; dichloromethane/methanol=19:1) $C_{12}H_{12}F_3N_3O_4$ (319.24) Mass spectrum: $(M-H)^-=318$ d. 4-[N-acetyl-N-(2-trifluoroacetylamino-ethyl)-amino]-aniline 0.7 g (2.1 mmol) of 4-[N-acetyl-N-(2-trifluoroacetylamino-ethyl)-amino]-nitrobenzene are dissolved in 20 ml of methanol and after the addition of 100 mg of 10% palladium on activated charcoal hydrogenated with hydrogen for 3 hours. Then the catalyst is filtered off and evaporated down.

Yield: 0.6 g (91% of theory), $R_f$ value: 0.7 (silica gel; dichloromethane/methanol/ammonia=9:1:0.1) $C_{12}H_{14}F_3N_3O_2$ (289.26) Mass spectrum: $(M-H)^-=288$, $(M+Na)^+=312$ The following compounds were prepared analogously to Example I:

(1) 4-[N-(2-dimethylamino-ethyl)-N-acetyl-amino]-aniline $R_f$ value: 0.3 (silica gel; dichloromethane/methanol/ammonia=9:1:0.1) $C_{12}H_{19}N_3O$ (221.31) Mass spectrum: $(M+H)^+=222$ (2) 4-[N-(2-acetylamino-ethyl)-N-acetyl-amino]-aniline $R_f$ value: 0.4 (silica gel; ethyl acetate/methanol=8:2) $C_{12}H_{17}N_3O_2$ (235.28) Mass spectrum: $(M+Na)^+=258$, $(M-H)^-=234$ (3) 4-[N-(2-acetylamino-ethyl)-N-propionyl-amino]-aniline $R_f$ value: 0.4 (silica gel; ethyl acetate/methanol=9:1)

(4) [N-(2-propionylamino-ethyl)-N-propionyl-amino]-aniline $R_f$ value: 0.5 (silica gel; ethyl acetate/methanol=9:1)

(5) 4-{N-[2-(N-acetyl-N-methyl-amino)-ethyl]-N-propionyl-amino}-aniline $R_f$ value: 0.5 (silica gel; dichloromethane/methanol/ammonia=19:1:0.1) $C_{14}H_{21}N_3O_2$ (263.34) Mass spectrum: $(M+Na)^+=286$ (6) 4-{N-[2-(N-acetyl-N-methyl-amino)-ethyl]-N-acetyl-amino}-aniline $R_f$ value: 0.3 (silica gel; ethyl acetate/methanol=9:1) $C_{13}H_{19}N_3O_2$ (249.31) Mass spectrum: $(M-H)^-=248$, $(M+Na)^+=272$ (7) 4-(dimethylaminocarbonylmethylamino)-aniline $R_f$ value: 0.6 (silica gel; dichloromethane/methanol/ammonia=9:1:0.1) $C_{10}H_{15}N_3O$ (193.25) Mass spectrum: $(M+H)^+=194$, $(M+Na)^+=216$ (8) 4-(N-ethoxycarbonylmethyl-N-acetyl-amino)-aniline $R_f$ value: 0.5 (silica gel; dichloromethane/methanol/ammonia=9:1:0.1) $C_{12}H_{16}N_2O_3$ (236.27) Mass spectrum: $(M-H)^-=235$, $(M+Na)^+=259$ (9) 4-[N-(3-dimethylamino-propyl)-N-propionyl-amino]-aniline $R_f$ value: 0.2 (silica gel; dichloromethane/methanol/ammonia=8.5:1.5:0.15) $C_{14}H_{23}N_3O$ (249.36) Mass spectrum: $(M-H)^-=248$, $(M+H)^+=250$

EXAMPLE II

4-[N-(2-benzyloxycarbonylamino-ethyl)-N-acetyl-amino]-aniline 450 mg (1.26 mmol) of 4-[N-(2-benzyloxycarbonylamino-ethyl)-N-acetyl-amino)-nitrobenzene (prepared analogously to Example I) are dissolved in 20 ml of methanol and after the addition of 100 mg of Lindlar catalyst hydrogenated for 2 hours with hydrogen. The catalyst is filtered off, the solution is evaporated down.

Yield: 410 mg (99% of theory), $R_f$ value: 0.4 (silica gel; ethyl acetate/dichloromethane=7:3) $C_{18}H_{21}N_3O_3$ (327.38) Mass spectrum: $(M+Na)^+=350$, $(M-H)^-=326$ The following compounds were prepared analogously to Example II:

(1) 4-{N-[2-(N-benzyl-N-methyl-amino)-ethyl]-N-acetyl-amino}-aniline $R_f$ value: 0.7 (silica gel; ethyl acetate/methanol/ammonia=9:1:0.1) $C_{18}H_{23}N_3O$ (297.40) Mass spectrum: $(M+H)^+=298$, $(M-H)^-=296$ (2) 4-{N-[2-(N-benzyl-N-methyl-amino)-ethyl]-N-propionyl-amino}-aniline $R_f$ value: 0.5 (silica gel; dichloromethane/methanol/ammonia=9:1:0.1) $C_{19}H_{25}N_3O$ (311.43) Mass spectrum: $(M+H)^+=312$

EXAMPLE III

4-[N-(2-trifluoroacetylamino-ethyl)-N-methylsulphonyl-amino]-aniline a. 4-(N-ethoxycarbonylmethyl-N-methylsulphonyl-amino)-nitrobenzene 20 g (92.5 mmol) of 4-(methylsulphonylamino)-nitroaniline are dissolved in 155 ml of DMSO and while cooling with ice 11.7 (104 mmol) of potassium tert. butoxide are added. After 1 hour 13.5 ml (121 mmol) of ethyl bromoacetate are added. The mixture is stirred for 18 hours at ambient temperature and the reaction solution is then poured onto ice water. It is extracted with ethyl acetate. The organic phase is washed with water, dried and freed from the solvent in vacuo. The residue is triturated with petroleum ether.

Yield: 27.1 g (97% of theory), Melting point: 73–75° C. $R_f$ value: 0.8 (silica gel; dichloromethane/ethyl acetate=9:1) $C_{11}H_{14}N_2O_6S$ (302.31) Mass spectrum: $(M+Na)^+=325$, $(M-H)^-=301$ b. 4-(N-carboxymethyl-N-methylsulphonyl-amino)-nitrobenzene 26.8 g (88.6 mmol) of 4-(N-ethoxycarbonylmethyl-N-methylsulphonyl-amino)-nitrobenzene are suspended in 320 ml of ethanol and combined with 268 ml of 1 N sodium hydroxide solution. The mixture is stirred for one hour at ambient temperature and then 268 ml of 1 N hydrochloric acid are added. The precipitate formed is suction filtered, washed with a little ethanol and ether, and dried in vacuo.

Yield: 21.9 g (90% of theory), Melting point: 215–218° C. $R_f$ value: 0.6 (silica gel; dichloromethane/methanol/glacial acetic acid=9:1:0.1) $C_9H_{10}N_2O_6S$ (274.25) Mass spectrum: $(M-H)^-=273$ c. 4-(N-aminocarbonylmethyl-N-methylsulphonyl-amino)-nitrobenzene 2.5 g (15.4 mmol) of CDI are added to a solution of 3 g (10.9 mmol) of 4-(N-carboxymethyl-N-methylsulphonyl-amino)-nitrobenzene in 30 ml of DMF. The mixture is stirred for one hour at ambient temperature. Then $NH_3$ is piped in at 0° C. over a period of 10 min. After 2 hours' stirring at ambient temperature 100 ml of water are added. The mixture is extracted with ethyl acetate, the organic phase is washed with water, dried over magnesium sulphate and evaporated to dryness. The residue is stirred with water, suction filtered and washed with ether.

Yield: 2.3 g (78% of theory), Melting point: 160° C. $R_f$ value: 0.5 (silica gel; ethyl acetate/dichloromethane=3:2)

d. 4-[N-(2-aminoethyl)-N-methylsulphonyl-amino]-nitrobenzene 2.3 g (8.4 mmol) of 4-(N-aminocarbonylmethyl-N-methylsulphonyl-amino)-nitrobenzene are refluxed in 35 ml (35 mmol) of borane-THF (1 M solution in THF) 7 hours. Then 30 ml of 6 N hydrochloric acid are added, and the mixture is refluxed for another 8 hours. The solvent is distilled off, the residue is mixed with water and extracted with ethyl acetate. The aqueous phase is made alkaline with potassium carbonate and extracted with dichloromethane. The organic phase is separated off, dried and evaporated down.

Yield: 1.7 g (77% of theory), $R_f$ value: 0.5 (silica gel; dichloromethane/methanol/ammonia=9:1:0.1) $C_9H_{13}N_3O_4S$ (259.29) Mass spectrum: $(M+H)^+=260$, $(M-H)^-=258$ e. 4-[N-(2-trifluoroacetylamino-ethyl)-N-methylsulphonyl-amino]-aniline Prepared analogously to Example Ib by reacting 4-[N-(2-aminoethyl)-N-methylsulphonyl-amino]-nitrobenzene with trifluoroacetic acid anhydride in trifluoroacetic acid followed by catalytic reduction analogously to Example Id with 10% palladium/charcoal in methanol.

Yield: 76% of theory, $R_f$ value: 0.6 (silica gel; dichloromethane/methanol/ammonia=9:1:0.1)

The following compounds were prepared analogously to Example III:

(1) 4-(N-ethoxycarbonylmethyl-N-ethylsulphonyl-amino)-aniline $R_f$ value: 0.5 (silica gel; petroleum ether/ethyl acetate=4:6) Melting point: 78° C. $C_{12}H_{18}N_2O_4S$ (286.35) Mass spectrum: $(M+Na)^+=309$, $(2M+Na)^+=593$ (2) 4-{N-[2-(N-acetyl-N-methyl-amino)-ethyl]-N-methylsulphonyl-amino)-aniline $R_f$ value: 0.5 (silica gel; dichloromethane/methanol/ammonia=19:1:0.1)

(3) 4-[N-(2-acetylamino-ethyl)-N-methylsulphonyl-amino]-aniline $R_f$ value: 0.5 (silica gel; dichloromethane/methanol/ammonia=19:1:0.1) $C_{11}H_{17}N_3O_3S$ (271.34) Mass spectrum: $(M+H)^+=272$, $(M+Na)^+=294$ (4) 4-{N-[2-(N-acetyl-N-methyl-amino)-ethyl]-N-ethylsulphonyl-amino}-aniline $R_f$ value: 0.5 (silica gel; dichloromethane/methanol/ammonia=19:1:0.1) Melting point: 140° C. $C_{13}H_{21}N_3O_3S$ (299.39) Mass spectrum: $M^+=299$ (5) 4-[N-(2-acetylamino-ethyl)-N-ethylsulphonyl-amino)-aniline $R_f$ value: 0.4 (silica gel; dichloromethane/methanol/ammonia=19:1:0.1) $C_{12}H_{19}N_3O_3S$ (285.36) Mass spectrum: $(M-H)^-=284$, $(M+Na)^+=308$ (6) 4-{N-[2-(N-methyl-N-trifluoroacetyl-amino)-ethyl]-N-methylsulphonyl-amino}-aniline $R_f$ value: 0.5 (silica gel; dichloromethane/ethyl acetate=9:1)

EXAMPLE IV

4-[N-(2-dimethylamino-ethyl)-N-phenylsulphonyl-amino]-aniline a. N-(2-dimethylamino-ethyl)-phenylsulphonamide 2.8 g (30 mmol) of N,N-dimethylethylenediamine are placed in 100 ml of dichloromethane and 8.3 ml (60 mmol) of triethylamine. While cooling with ice a solution of 3.9 ml (30 mmol) of benzenesulphonic acid chloride in 100 ml of dichloromethane is added dropwise and the mixture is stirred overnight at ambient temperature. Water is added and the mixture is extracted with dichloromethane. The organic phase is dried and evaporated down.

Yield: 6.8 g (99% of theory), $R_f$ value: 0.4 (silica gel; dichloromethane/methanol/ammonia=9:1:0.1) $C_{10}H_{16}N_2O_2S$ (228.23) Mass spectrum: $(M-H)^-=227$, $(M+H)^+=229$ b. 4-[N-(2-dimethylamino-ethyl)-N-phenylsulphonyl-amino]-nitrobenzene 6.8 g (29.8 mmol) of N-(2-dimethylamino-ethyl)-phenylsulphonamide are dissolved in 100 ml of DMF and combined with 1.3 g (30 mmol) of sodium hydride (55% in oil). The mixture is stirred for one hour at ambient temperature. Then 4.2 g (29.8 mmol) of 4-fluoro-nitrobenzene are added, and stirring is continued for another 16 hours. After the addition of 300 ml of water the mixture is extracted with ethyl acetate. The organic phase is washed with water, dried and evaporated down. The residue is acidified with 1 N hydrochloric acid and washed with ethyl acetate. The aqueous phase is then made basic again with sodium hydroxide solution and extracted with ethyl acetate. The organic phase is dried and evaporated down.

Yield: 6.0 g (58% of theory), $R_f$ value: 0.4 (silica gel; dichloromethane/methanol/ammonia=9:1:0.1) $C_{16}H_{19}N_3O_4S$ (349.41) Mass spectrum: $(M-H)^-=348$, $(M+H)^+=350$ c. 4-[N-(2-dimethylaminoethyl)-N-phenylsulphonyl-amino]-aniline Prepared analogously to Example Id by catalytic hydrogenation of 6 g (17.2 mmol) of 4-[N-(2-dimethylamino-ethyl)-N-phenylsulphonyl-amino]-nitrobenzene.

Yield: 5.5 g (99% of theory), $R_f$ value: 0.5 (silica gel; dichloromethane/methanol/ammonia=9:1:0.1) $C_{16}H_{21}N_3O_2S$ (319.43) Mass spectrum: $(M+H)^+=320$ The following compounds were prepared analogously to Example IV:

(1) 4-[N-(2-dimethylamino-ethyl)-N-propylsulphonyl-amino]-aniline $R_f$ value: 0.4 (silica gel; dichloromethane/methanol/ammonia=9:1:0.1) $C_{13}H_{23}N_3O_2S$ (285.41) Mass spectrum: $(M+H)^+=286$, $(M-H)^-=284$ (2) 4-[N-(2-dimethylamino-ethyl)-N-butylsulphonyl-amino]-aniline $R_f$ value: 0.4 (silica gel; dichloromethane/methanol/ammonia=9:1:0.1) $C_{14}H_{25}N_3O_2S$ (299.43) Mass spectrum: $(M+H)^+=300$ (3) 4-[N-(3-dimethylamino-propyl)-N-methylsulphonyl-amino]-aniline Melting point: 112–113° C. $R_f$ value: 0.4 (silica gel; dichloromethane/methanol/ammonia=9:1:0.1)
$C_{12}H_{21}N_3O_2S$ (271.38) Mass spectrum: $(M+H)^+=272$, $(M+Na)^+=294$ (4) 4-[N-(2-dimethylamino-ethyl)-N-benzylsulphonyl-amino]-aniline $R_f$ value: 0.3 (silica gel; dichloromethane/methanol/ammonia=9:1:0.1) $C_{17}H_{23}N_3O_2S$ (333.46) Mass spectrum: $(M+H)^+=334$, $(M+Na)^+=356$ (5) 3-chloro-4-[N-(2-dimethylamino-ethyl)-N-methylsulphonyl-amino]-aniline Melting point: 145–148° C. $R_f$ value: 0.5 (silica gel; dichloromethane/ethanol/ammonia=5:1:0.01)
$C_{11}H_{18}ClN_3O_2S$ (291.80) Mass spectrum: $(M+H)^+=294$, 292, $(M-H)^-=292$, 290

(6) 3-amino-4-[N-(2-dimethylamino-ethyl)-N-methylsulphonyl-amino]-aniline $R_f$ value: 0.3 (silica gel; dichloromethane/methanol/ammonia=9:1:0.1) $C_{11}H_{20}N_4O_2S$ (272.37) Mass spectrum: $(M+H)^+=273$ (7) 4-[N-(2-dimethylamino-ethyl)-N-methylsulphonyl-amino]-aniline $R_f$ value: 0.3 (silica gel; dichloromethane/methanol/ammonia=9:1:0.1) Melting point: 147–148° C. $C_{11}H_{19}N_3O_2S$ (257.36) Mass spectrum: $(M+H)^+=258$, $(M+Na)^+=280$

EXAMPLE V

3-[N-(2-dimethylamino-ethyl)-N-methylsulphonyl-amino]-aniline a. 3-[N-(2-dimethylamino-ethyl)-N-methylsulphonyl-amino]-nitrobenzene 5 g (23.1 mmol) of 3-methylsulphonylamino-nitrobenzene are dissolved in 50 ml of DMSO and combined with 6.5 g (58 mmol) of potassium tert. butoxide while cooling with ice. The solution thus obtained is added dropwise to a solution of 5 g (34.7 mmol) of 2-chloro-N,N-dimethyl-ethylamine in 30 ml of DMSO. The mixture is stirred for 2 hours at ambient temperature and then heated for 6 hours to 100° C. After cooling to ambient temperature 400 ml of water are added. The mixture is extracted with ethyl acetate. Water and 1 N hydrochloric acid are added to the combined organic phases until an acid reaction is obtained. The aqueous phase is washed with ethyl acetate. Then the aqueous phase is made alkaline with sodium carbonate and the product is extracted with ethyl acetate. Drying the combined organic phases over magnesium sulphate and eliminating the solvents in vacuo yields the product as a red oil.

Yield: 2.07 g (31% of theory), $R_f$ value: 0.3 (silica gel; ethyl acetate/methanol=4:1) $C_{11}H_{17}N_3O_4S$ (287.34) Mass spectrum: $(M-H)^-=286$, $(M+H)^+=288$ b. 3-[N-(2-dimethylamino-ethyl)-N-methylsulphonyl-amino]-aniline Prepared analogously to Example 1d by catalytic hydrogenation of 1.9 g (6.8 mmol) of 3-[N-(2-dimethylamino-ethyl)-N-methylsulphonyl-amino]-nitrobenzene over palladium/charcoal.

Yield: 1.8 g (99% of theory), $R_f$ value: 0.3 (silica gel; ethyl acetate/methanol/$NH_4OH$=8:2:0.1) $C_{11}H_{19}N_3O_2S$ (257.36) Mass spectrum: $(M-H)^-=256$, $(M+H)^+=258$

EXAMPLE VI 4-(4-benzyl-piperazinomethyl)-aniline a. 4-(4-tert.butoxycarbonyl-piperazinomethyl)-nitrobenzene A mixture of 10.6 g (57 mmol) of N-tert.butoxycarbonyl-piperazine, 10.8 g (62.7 mmol) of 4-nitrobenzylchloride, 23.8 ml (171 mmol) of triethylamine in 100 ml of dichloromethane is stirred for 12 hours at 70° C. After diluting with water the organic phase is separated off, dried and evaporated down.

Yield: 19 g (99% of theory), Melting point: 83–84° C. $R_f$ value: 0.7 (silica gel; dichloromethane/methanol/ammonia=9:1:0.1) $C_{16}H_{23}N_3O_4$ (321.38) Mass spectrum: $(M+H)^+=322$, $(M-H)^-=320$ b. 4-piperazinomethyl-nitrobenzene-dihydrochloride 6.4 g (20 mmol) of 4-(4-tert.butoxycarbonyl-piperazinomethyl)-nitrobenzene are dissolved in 20 ml of dichloromethane and combined with 40 ml of ethyl acetate/HCl. The reaction solution is diluted with ether, the precipitate formed is suction filtered as a crude product and then reacted further.

Yield: 5.4 g (92% of theory), Melting point: 257–258° C. $R_f$ value: 0.3 (silica gel; dichloromethane/methanol/ammonia=9:1:0.1)

c. 4-(4-benzylpiperazinomethyl)-nitrobenzene

The free base is produced from 1.5 g (5 mmol) of 4-piperazinomethyl-nitrobenzene-dihydrochloride by dissolving in 25 ml of 1 N sodium hydroxide solution, extracting with ethyl acetate and then eliminating the solvent in vacuo. The solid thus obtained is combined with 2.5 ml of 2 N acetic acid, 0.5 ml (5.5 mmol) of benzaldehyde and 50 ml of methanol and, after the addition of 0.7 g (5 mmol) of sodium cyanoborohydride, stirred for 2 hours. Then the pH is adjusted to acid with 1 N hydrochloric acid and the reaction solution is washed with ether. The aqueous phase is then made basic with sodium hydroxide solution. The product is extracted with ether, the combined ether extracts are dried and the solvent is eliminated in vacuo.

Yield: 1.3 g (84% of theory), $R_f$ value: 0.6 (silica gel; dichloromethane/methanol/ammonia=9:1:0.1) $C_{18}H_{21}N_3O_2$ (311.39) Mass spectrum: $(M+H)^+=312$ d. 4-(4-benzylpiperazinomethyl)-aniline Prepared analogously to Example Id by catalytic hydrogenation of 1.3 g (4.2 mmol) of 4-(4-benzylpiperazinomethyl)-nitrobenzene over palladium/charcoal.

Yield: 1.2 g (87% of theory), Melting point: 88–89° C. $C_{18}H_{23}N_3$ (281.4) Mass spectrum: $(M+H)^+=282$

EXAMPLE VII 4-(4-tert.butoxycarbonyl-piperazinomethyl)-aniline a. 4-(4-tert.butoxycarbonyl-piperazinomethyl)-nitrobenzene 10.6 g (57 mmol) of N-tert.butoxycarbonyl-piperazine are dissolved in 100 ml of dichloromethane and combined with 10.7 g (63 mmol) of 4-nitrobenzylchloride and 24 ml (171 mmol) of triethylamine. The mixture is refluxed for 12 hours. After cooling to ambient temperature the reaction solution is washed several times with water. The organic phase is dried over magnesium sulphate and then evaporated to dryness.

Yield: 17 g (99%) of theory Melting point: 83–84° C. $R_f$ value: 0.7 (silica gel; dichloromethane/methanol/ammonia=9:1:0.1) $C_{16}H_{23}N_3O_4$ (321.38) Mass spectrum: $(M+H)^+=322$, $(M-H)^-=320$ b. 4-(4-tert.butoxycarbonyl-piperazinomethyl)-aniline Prepared analogously to Example Id by catalytic hydrogenation of 4-(4-tert.butoxycarbonyl-piperazinomethyl)-nitrobenzene with Raney nickel in ethyl acetate/methanol (1:1).

Melting point: 106–107° C. $R_f$ value: 0.6 (silica gel; dichloromethane/methanol/ammonia=9:1:0.1) $C_{16}H_{25}N_3O_2$ (291.39) Mass spectrum: $(M+H)^+=292$, $(M+Na)^+=314$ The following compounds were prepared analogously to Example VII:

(1) 4-(pyrrolidin-1-yl-methyl)-aniline $R_f$ value: 0.2 (silica gel; dichloromethane/methanol/$NH_4OH$=5:1:0.01) Melting point: 48–50° C.

(2) 4-(4-methylpiperazinomethyl)-aniline

Melting point: 94–95° C. $R_f$ value: 0.2 (silica gel; dichloromethane/methanol/ammonia=9:1:0.1) $C_{12}H_{19}N_3$ (205.31) Mass spectrum: $(M+H)^+=206$ (3) 3-(dimethylaminomethyl)-aniline $R_f$ value: 0.7 (silica gel; ethyl acetate) Melting point: 43–46° C.

(4) 4-(dimethylaminomethyl)-aniline $R_f$ value: 0.13 (silica gel; ethyl acetate/ethanol=8:2)

(5) 4-(2-dimethylamino-ethyl)-aniline $R_f$ value: 0.3 (silica gel; dichloromethane/methanol/ammonia=19:1:0.1) Melting point: 40° C. $C_{10}H_{16}N_2$ (164.25) Mass spectrum: $(M+H)^+=165$ (6) 4-(N-benzyl-N-methyl-aminomethyl)-aniline $R_f$ value: 0.5 (silica gel; dichloromethane/methanol/ammonia=10:1:0.01) Melting point: 48–50° C. $C_{15}H_{18}N_2$ (226.32) Mass spectrum: $(M+H)^+=227$ (7) 4-piperidinomethyl-aniline $R_f$ value: 0.2 (silica gel; dichloromethane/methanol/ammonia=9:1:0.1) Melting point: 88–89° C.

(8) 4-(2,6-dimethylpiperidino-methyl)-aniline $R_f$ value: 0.3 (silica gel; dichloromethane/methanol/ammonia=5:1:0.01) Melting point: 112–115° C.

(9) 4-(N-ethyl-N-methyl-aminomethyl)-aniline $R_f$ value: 0.4 (silica gel; dichloromethane/methanol/ammonia=10:1:0.1) $C_{10}H_{16}N_2$ (164.25) Mass spectrum: $(M+H)^+=165$

(10) 4-[4-(3-trifluoromethylcarbonylamino-propyl)-piperidinomethyl]-aniline $R_f$ value: 0.4 (silica gel; dichloromethane/methanol/ammonia=10:1:0.1) $C_{17}H_{24}F_3N_3O$ (343.40) Mass spectrum: $(M+H)^+=344$

(11) 4-(N-tert.butoxycarbonyl-N-propyl-aminomethyl)-aniline $C_{15}H_{24}N_2O_2$ (264.37) Mass spectrum: $(M+Na)^+=287$

(12) 4-(N-tert.butoxycarbonyl-N-butyl-aminomethyl)-aniline $R_f$ value: 0.19 (silica gel; dichloromethane/methanol=50:1) $C_{16}H_{26}N_2O_2$ (278.40) Mass spectrum: $(M+Na)^+=301$

(13) 4-(N-tert.butoxycarbonyl-N-ethyl-aminomethyl)-aniline

Melting point: 85° C. $R_f$ value: 0.3 (silica gel; dichloromethane/methanol/=50:1) $C_{14}H_{22}N_2O_2$ (250.34) Mass spectrum: $(M+Na)^+=273$

EXAMPLE VIII 4-(2-oxopiperidinomethyl)-aniline 6.4 g (42 mmol) of 4-nitrobenzaldehyde are dissolved in 150 ml of methanol and combined with 4.9 g (42 mmol) of 5-aminovaleric acid and 1.8 g (29 mmol) of sodium cyanoborohydride. The mixture is stirred for 18 hours at ambient temperature and then carefully mixed with 20 ml of conc. hydrochloric acid. The solvent is eliminated in vacuo, the residue is taken up in water and extracted with dichloromethane. The residue obtained after evaporation is chromatographed on silica gel (dichloromethane/methanol, 4:1). A mixture of methyl 5-(4-nitrobenzylamino)-pentanoate and 4-(2-oxopiperidinomethyl)-nitrobenzene is obtained which is dissolved in 100 methanol and combined with 50 ml of 1 N sodium hydroxide solution. The mixture is stirred for one hour at ambient temperature, 50 ml of 1 N hydrochloric acid are added and the reaction solution is evaporated down to 100 ml. The aqueous phase thus obtained is extracted with dichloromethane. The combined organic phases are dried over sodium sulphate and evaporated to dryness.

The residue is hydrogenated analogously to Example Id over Raney nickel in methanol under a hydrogen atmosphere of 3 bar for 11 hours.

Total yield: 2.2 g (26% of theory), $R_f$ value: 0.63 (silica gel; dichloromethane/methanol=9:1)

EXAMPLE IX 4-(N-piperidinomethylcarbonyl-N-methyl-amino)-aniline a. 4-(N-bromomethylcarbonyl-N-methyl-amino)-nitrobenzene 23.5 g (0.15 mol) of N-methyl-4-nitroaniline are dissolved in 400 ml of dioxane and combined with 22.2 g (0.3 mol) of lithium carbonate. Then 32.2 g (0.18 mol) of bromoacetylbromide are added dropwise in such a way that the internal temperature does not exceed 33° C. After 18 hours' stirring the reaction solution is evaporated down to 100 ml, combined with 500 ml of water and stirred for 1 hour. The precipitate formed is suction filtered, washed with water and dried. The crude product is stirred in 400 ml of ethyl acetate at 40° C. Then the insoluble matter is filtered off, the solution is evaporated down and the solid residue is triturated with ether.

Yield: 35 g (83% of theory), Melting point: 85–87° C.

b. 4-(N-piperidinomethylcarbonyl-N-methyl-amino)-nitrobenzene 5.4 g (20 mmol) of 4-(N-bromomethylcarbonyl-N-methyl-amino)-nitrobenzene are dissolved in 100 ml of acetone and combined with 5.5 g (40 mmol) of potassium carbonate. 3 ml (30 mmol) of piperidine are slowly added dropwise and the mixture is stirred for 18 hours at ambient temperature. The reaction solution is filtered, and the filtrate is evaporated to dryness. The residue is dissolved in ethyl acetate, washed with water, dried over magnesium sulphate and evaporated to dryness.

Yield: 5.6 g (99% of theory).

c. 4-(N-piperidinomethylcarbonyl-N-methyl-amino)-aniline

Prepared analogously to Example Id by catalytic hydrogenation of 4-(N-piperidinomethylcarbonyl-N-methyl-amino)-nitrobenzene in methanol over palladium/charcoal.

Yield 4.95 g (99% of theory)

EXAMPLE X

4-(tert.butoxycarbonylaminomethyl)-aniline 20 g (164 mmol) of 4-aminobenzylamine and 20.2 g (210 mmol) of triethylamine are dissolved in 100 ml of dioxane and 50 ml of water. 35.8 g (165 mmol) of di-tert.butyl-dicarbonate dissolved in 60 ml of dioxane are added to this solution while cooling with ice and the resulting mixture is stirred for 18 hours at ambient temperature. Then the solvent is distilled off in vacuo, the residue is distributed in ethyl acetate/water. The combined organic extracts are freed from solvent in vacuo. The crude product is heated in 200 ml of petroleum ether, cooled slowly with vigorous stirring and the crystalline product is removed by suction filtering.

Yield: 34.8 g (96% of theory), Melting point: 77–78° C.

EXAMPLE XI

4-(1H-imidazol-2-yl)-aniline 7.2 g (50 mmol) of 2-phenylimidazol are dissolved in 100 ml of conc. sulphuric acid. While cooling with ice 5.0 g (62 mmol) of ammonium nitrate are added in batches and the mixture is stirred for 2.5 hours. The reaction solution is then poured onto ice, made basic with conc. ammonia and the crystalline product is suction filtered. The nitro compound thus obtained is catalytically hydrogenated analogously to Example Id in DMF over palladium/charcoal.

Yield: 24% of theory, $R_f$ value: 0.4 (silica gel; dichloromethane/methanol/ammonia=9:1:0.1)

EXAMPLE XII

Pyridine-2-sulphonic acid chloride 5.0 g (45 mmol) of pyridine-2-thiol are dissolved in 40 ml of conc. hydrochloric acid. While the solution is cooled with ice, chlorine gas is piped in over a period of 2.5 hours. In order to destroy any excess gas a washing bottle containing 1 N sodium thiosulphate solution is attached. Then the reaction solution is poured onto ice water and extracted with ether and dichloromethane. The organic phases are combined, dried and freed from solvent in vacuo. The crude product is further reacted immediately.

Yield: 8 g (100% of theory).

EXAMPLE XIII

Pyridine-3-sulphonic acid chloride hydrochloride 1 g (6.3 mmol) of pyridine-3-sulphonic acid and 1.4 g (6.7 mmol) of phosphorus pentachloride are stirred for 2 hours at 150° C. After cooling, excess phosphorus pentachloride is eliminated in vacuo. The crude product is further reacted immediately.

Yield: 1.2 g (91% of theory).

Preparation of the End Products:

EXAMPLE 1

(Z)-3-{1-[4-(N-acetyl-N-(2-aminoethyl)-amino)-phenylamino]-1-phenyl-methylidene}-5-phenylsulphonylamino-2-indolinone a. 1-acetyl-2-indolinone 13.3 g (0.1 mol) of 2-indolinone and 30 ml of acetic anhydride are stirred for 3 hours at 170° C. After cooling the mixture is combined with 150 ml of ice water, the crystalline product is suction filtered, washed with water and dried.

Yield: 16.6 g (95% of theory), Melting point: 129–130° C.

b. 1-acetyl-5-nitro-2-indolinone 0.5 g (2.8 mmol) of 1-acetyl-2-indolinone are placed in 4 ml of conc. sulphuric acid. At a temperature of −10 to −5° C., 0.3 g (3.4 mmol) of ammonium nitrate are added in batches. After 45 minutes the mixture is poured onto ammonia/ice water, the crystalline precipitate is suction filtered, washed with water and dried. The crude product is recrystallised from 70 ml of cyclohexane.

Yield: 0.2 g (32% of theory), Melting point: 150–157° C. $R_f$ value: 0.7 (silica gel; cyclohexane/ethyl acetate=4:6)

c. 1-acetyl-5-amino-2-indolinone 30.0 g (136 mmol) of 1-acetyl-5-nitro-2-indolinone are dissolved in a mixture of 650 ml of dichloromethane and 650 ml of methanol and after the addition of 5 g of 10% palladium on activated charcoal the mixture is hydrogenated for 45 minutes with hydrogen. Then the catalyst is filtered off and evaporated down.

Yield: 22.4 g (87% of theory), Melting point: 177° C. $R_f$ value: 0.7 (silica gel; ethyl acetate) $C_{10}H_{10}N_2O_2$ (190.20) Mass spectrum: $(M-H)^-=189$, $(M+Na)^+=213$ d. 1-acetyl-5-phenylsulphonylamino-2-indolinone 20.0 g (105 mmol) of 1-acetyl-5-amino-2-indolinone are placed in 200 ml of pyridine, combined with 15.3 ml (120 mmol) of benzenesulphonic acid chloride while cooling with ice and stirred for 2 hours. Then the mixture is poured onto 1.8 l of water and suction filtered. The crude product is stirred into acetone, suction filtered and dried.

Yield: 30.5 g (88% of theory), Melting point: 245° C. $R_f$ value: 0.5 (silica gel; dichloromethane/ethyl acetate=9:1) $C_{16}H_{14}N_2O_4S$ (330.37) Mass spectrum: $(M-H)^-=329$, $(M+Na)^+=353$ e. 1-acetyl-3-(1-ethoxy-1-phenyl-methylidene)-5-(N-acetyl-N-phenylsulphonyl-amino)-2-indolinone 8.0 g (24.2 mmol) of 1-acetyl-5-phenylsulphonylamino-2-indolinone are dissolved in 150 ml of acetic anhydride and after the addition of 20 ml (88.1 mmol) of triethyl orthobenzoate refluxed for 6 hours. The solvent is distilled off, the residue is triturated with ether, suction filtered and dried.

Yield: 7.8 g (64% of theory), Melting point: 237° C. $R_f$ value: 0.7 (silica gel; dichloromethane/ethyl acetate=19:1) $C_{27}H_{24}N_2O_6S$ (504.57) Mass spectrum: $M^+=504$ f. (Z)-3-{1-[4-(N-acetyl-N-(2-aminoethyl)-amino)-phenylamino]-1-phenyl-methylidene}-5-phenylsulphonylamino-2-indolinone A mixture of 0.5 g (1 mmol) of 1-acetyl-3-(1-ethoxy-1-phenyl-methylidene)-5-(N-acetyl-N-phenylsulphonyl-amino)-2-indolinone and 0.3 g (1.2 mmol) of 4-[N-acetyl-N-(2-trifluoroacetylamino-ethyl)-amino]-aniline are stirred in 5 ml of DMF for 6 hours at 120° C. After cooling to ambient temperature 5 ml of methanol and 3 ml (6 mmol) of 2 N sodium hydroxide solution are added, and the mixture is stirred for 30 minutes. The reaction mixture is diluted with 50 ml of water and the crystalline precipitate is suction filtered and dried. The residue is chromatographed on silica gel (dichloromethane/methanol/ammonia=9:1:0.1).

Yield: 0.3 g (49% of theory), Melting point: 216° C. $R_f$ value: 0.3 (silica gel; dichloromethane/methanol/ammonia=9:1:0.1) $C_{31}H_{29}N_5O_4S$ (567.67) Mass spectrum: $(M-H)^-=566$, $(M+H)^+=568$

EXAMPLES 2 TO 97

Using the intermediate products prepared in Examples I to XIII, the compounds of formula IA of Examples 2 to 97 listed in Table I are prepared analogously to Example 1.

TABLE I

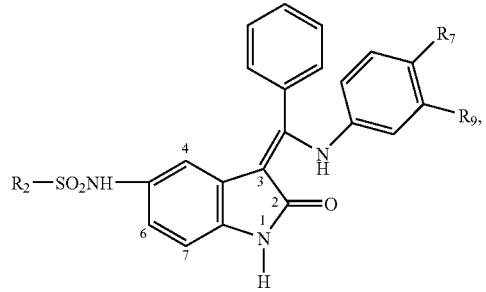
(IA)

| Example | $R_2$ | $R_7$ | $R_9$ | chemical name | Melting point (° C.) |
|---|---|---|---|---|---|
| | phenyl | N-(2-aminoethyl)-N-methylsulphonyl-amino | H | (Z)-3-{1-[4-(N-(2-aminoethyl)-N-methylsulphonyl-amino)-phenylamino]-1-phenyl-methylidene}-5-phenylsulphonylamino-2-indolinone | 245 |
| | phenyl | N-(2-methylamino-ethyl)-N-methylsulphonyl-amino | H | (Z)-3-{1-[4-(N-(2-methylamino-ethyl)-N-methylsulphonyl-amino)-phenylamino]-1-phenyl-methylidene}-5-phenylsulphonylamino-2-indolinone | 227–229 |
| | phenyl | N-(2-dimethylamino-ethyl)-N-phenylsulphonyl-amino | H | (Z)-3-{1-[4-(N-(2-dimethylaminoethyl)-N-phenylsulphonyl-amino)-phenylamino)-1-phenyl-methylidene}-5-phenylsulphonylamino-2-indolinone | 168–169 |
| | phenyl | N-(2-dimethylamino-ethyl)-N-propylsulphonyl-amino | H | (Z)-3-{1-[4-(N-(2-dimethylamino-ethyl)-N-propylsulphonyl-amino)-phenylamino]-1-phenyl-methylidene}-5-phenylsulphonylamino-2-indolinone | 137–138 |
| | phenyl | N-(2-dimethylamino-ethyl)-N-butylsulphonyl-amino | H | (Z)-3-{1-[4-(N-(2-dimethylamino-ethyl)-N-butylsulphonyl-amino)-phenylamino]-1-phenyl-methylidene}-5-phenylsulphonylamino-2-indolinone | 197–198 |
| | phenyl | 4-benzyl-piperazino-methyl | H | (Z)-3-{1-[4-(4-benzyl-piperazinomethyl)-phenylamino]-1-phenyl-methylidene}-5-phenylsulphonylamino-2-indolinone | 130 (decomp.) |
| | phenyl | N-acetyl-N-(2-benzyl-oxycarbonylamino-ethyl)-amino | H | (Z)-3-{1-[4-(N-acetyl-N-(2-benzyloxycarbonylamino-ethyl)-amino)-phenylamino]-1-phenyl-methylidene}-5-phenylsulphonyl-amino-2-indolinone | 180 |
| | phenyl | 4-methylpiperazino-methyl | H | (Z)-3-{1-[4-(4-methylpiperazinomethyl)-phenylamino]-1-phenyl-methylidene}-5-phenylsulphonylamino-2-indolinone | 243–244 |
| | phenyl | morpholinomethyl | H | (Z)-3-{1-[4-(morpholinomethyl)-phenylamino]-1-phenyl-methylidene}-5-phenylsulphonylamino-2-indolinone | 243–244 |
| | phenyl | 2-oxopiperidinomethyl | H | (Z)-3-{1-[4-(2-oxopiperidinomethyl)-phenylamino]-1-phenyl-methylidene}-5-phenylsulphonylamino-2-indolinone | 311–312 |
| | phenyl | pyrrolidin-1-ylmethyl | H | (Z)-3-{1-[4-(pyrrolidin-1-ylmethyl)-phenylamino]-1-phenyl-methylidene}-5-phenylsulphonylamino-2-indolinone | 228–229 |
| | phenyl | 4-tert.butoxycarbonyl-piperazinomethyl | H | (Z)-3-{1-[4-(4-tert.butoxycarbonyl-piperazinomethyl)-phenylamino]-1-phenyl-methylidene}-5-phenylsulphonylamino-2-indolinone | 160–161 |
| | phenyl | N-methyl-N-formyl-amino | H | (Z)-3-{1-[4-(N-methyl-N-formyl-amino)-phenylamino]-1-phenyl-methylidene}-5-phenylsulphonylamino-2-indolinone | 315–317 |
| | phenyl | tert.butoxycarbonyl-amino | H | (Z)-3-[1-(4-tert.butoxycarbonylamino-phenylamino)-1-phenyl-methylidene]-5-phenylsulphonylamino-2-indolinone | 96–98 |
| | phenyl | N-methyl-N-propionyl-amino | H | (Z)-3-{1-[4-(N-methyl-N-propionyl-amino)-phenylamino]-1-phenyl-methylidene}-5-phenylsulphonylamino-2-indolinone | 208–210 |
| | phenyl | acetylamino | H | (Z)-3-[1-(4-acetylamino-phenylamino)-1-phenyl-methylidene]-5-phenylsulphonylamino-2-indolinone | 245–247 |
| | phenyl | N-methyl-N-ethylsulphonyl-amino | H | (Z)-3-{1-[4-(N-methyl-N-ethylsulphonyl-amino)-phenylamino]-1-phenyl-methylidene}-5-phenylsulphonylamino-2-indolinone | 278–280 |

TABLE I-continued

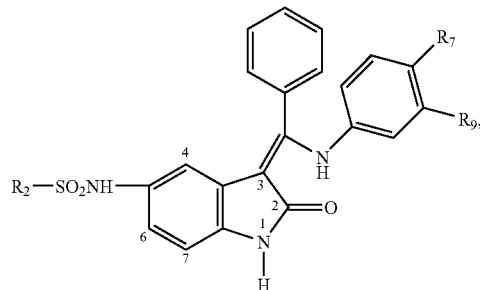

(IA)

| Example | $R_2$ | $R_7$ | $R_9$ | chemical name | Melting point (° C.) |
|---|---|---|---|---|---|
| | phenyl | propionylamino | H | (Z)-3-[1-(4-propionylamino-phenylamino)-1-phenyl-methylidene]-5-phenylsulphonylamino-2-indolinone | 254–256 |
| | phenyl | N-methyl-N-acetyl-amino | H | (Z)-3-{1-[4-(N-methyl-N-acetyl-amino)-phenylamino]-1-phenyl-methylidene}-5-phenylsulphonylamino-2-indolinone | 283–285 |
| | phenyl | N-aeetyl-N-[2-(N-benzyl-N-methyl-amino)-ethyl]-amino | H | (Z)-3-{1-[4-(N-acetyl-N-(2-(N-benzyl-N-methyl-amino)-ethyl)-amino)-phenylamino]-1-phenyl-methylidene}-5-phenylsulphonylamino-2-indolinone | 237 |
| | phenyl | H | H | (Z)-3-(1-phenylamino-1-phenyl-methylidene)-5-phenylsulphonylamino-2-indolinone | 283 |
| | phenyl | chloro | H | (Z)-3-[1-(4-chlorophenylamino)-1-phenyl-methylidene]-5-phenylsulphonylamino-2-indolinone | 295 |
| | phenyl | N-(2-dimethylamino-ethyl)-N-methylsuiphonyl-amino | H | (Z)-3-{1-[4-(N-(2-dimethylamino-ethyl)-N-methylsulphonyl-amino)-phenylamino]-1-phenyl-methylidene}-5-phenylsulphonylamino-2-indolinone | 234 |
| | phenyl | N-(2-dimethylamino-ethyl)-N-acetyl-amino | H | (Z)-3-{1-[4-(N-(2-dimethylamino-ethyl)-N-acetyl-amino)-phenylamino]-1-phenyl-methylidene}-5-phenylsulphonylamino-2-indolinone | 202 |
| | phenyl | N-piperidinomethyl-carbonyl-N-methyl-amino | H | (Z)-3-{1-[4-(N-piperidinomethylcarbonyl-N-methyl-amino)-phenylamino]-1-phenyl-methylidene}-5-phenylsulphonylamino-2-indolinone | 269 |
| | phenyl | H | N-(2-dimethylamino-ethyl)-N-methyl-sulphonyl-amino | (Z)-3-{1-[3-(N-(2-dimethylamino-ethyl)-N-methylsulphonyl-amino)-phenylamino]-1-phenyl-methylidene}-5-phenylsulphonylamino-2-indolinone | 140 |
| | phenyl | H | dimethylamino-methyl | (Z)-3-[1-(3-dimethylaminomethyl-phenylamino)-1-phenyl-methylidene]-5-phenylsulphonylamino-2-indolinone | 140 |
| | phenyl | N-(2-acetylamino-ethyl)-N-acetyl-amino | H | (Z)-3-{1-[4-(N-(2-acetylamino-ethyl)-N-acetyl-amino)-phenylamino]-1-phenyl-methylidene}-5-phenylsulphonylamino-2-indolinone | 229 |
| | phenyl | N-(2-acetylamino-ethyl)-N-propionyl-amino | H | (Z)-3-{1-[4-(N-(2-acetylamino-ethyl)-N-propionyl-amino)-phenylamino]-1-phenyl-methylidene}-5-phenylsulphonylamino-2-indolinone | 278 |
| | phenyl | N-(2-propionylamino-ethyl)-N-propionyl-amino | H | (Z)-3-{1-[4-(N-(2-propionylamino-ethyl)-N-propionyl-amino)-phenylamino]-1-phenyl-methylidene}-5-phenylsulphonylamino-2-indolinone | 280 |
| | phenyl | N-[2-(N-acetyl-N-methyl-amino)-ethyl]-N-methylsulphonyl-amino | H | (Z)-3-{1-[4-(N-(2-(N-acetyl-N-methyl-amino)-ethyl)-N-methylsulphonyl-amino)-phenylamino]-1-phenyl-methylidene}-5-phenylsulphonylamino-2-indolinone | 180 (decomp.) |
| | phenyl | N-(2-acetylamino-ethyl)-N-methylsulphonyl-amino] | H | (Z)-3-{1-[4-(N-(2-acetylamino-ethyl)-N-methylsulphonyl-amino)-phenylamino]-1-phenyl-methylidene}-5-phenylsulphonylamino-2-indolinone | 171 |
| | phenyl | 4-{N-[2-(N-acetyl-N-methyl-amino)-ethyl]-N-ethylsulphonyl-amino | H | (Z)-3-{1-[4-(N-(2-(N-acetyl-N-methyl-amino)-ethyl)-N-ethylsulphonyl-amino)-phenylamino]-1-phenyl-methylidene}-5-phenylsulphonylamino-2-indolinone | 216 |
| | phenyl | cyano | H | (Z)-3-[1-(4-cyanophenylamino)-1-phenyl-methylidene]-5-phenylsulphonylamino-2-indolinone | 291–293 |
| | phenyl | dimethylaminomethyl | H | (Z)-3-[1-(4-dimethylaminomethyl-phenylamino)-1-phenyl-methylidene]-5-phenylsulphonylamino-2-indole | 255–256 |
| | phenyl | 2-dimethylamino-ethyl | H | (Z)-3-[1-(4-(2-dimethylamino-ethyl)-phenylamino)-1-phenyl-methylidene]-5-phenylsulphonylamino-2-indolinone | 302–303 |

TABLE I-continued

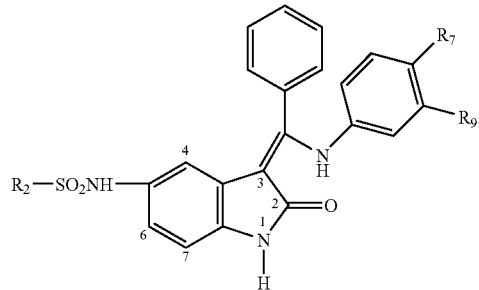

(IA)

| Example | R$_2$ | R$_7$ | R$_9$ | chemical name | Melting point (° C.) |
|---|---|---|---|---|---|
| | phenyl | N-(2-acetylamino-ethyl)-N-ethylsulphonyl-amino | H | (Z)-3-{1-[4-(N-(2-acetylamino-ethyl)-N-ethylsulphonyl-amino)-phenylamino]-1-phenyl-methylidene}-5-phenylsulphonylamino-2-indolinone | 158 |
| | phenyl | acetylaminomethyl | H | (Z)-3-[1-(4-acetylaminomethyl-phenylamino)-1-phenyl-methylidene]-5-phenylsulphonylamino-2-indolinone | 289–290 |
| | phenyl | N-[2-(N-acetyl-N-methyl-amino)-ethyl]-N-acetyl-amino | H | (Z)-3-{1-[4-(N-(2-(N-acetyl-N-methyl-amino)-ethyl)-N-acetyl-amino)-phenylamino]-1-phenyl-methylidene}-5-phenylsulphonylamino-2-indolinone | 297 |
| | phenyl | methylsulphonylamino | H | (Z)-3-[1-(4-methylsulphonylamino-phenylamino)-1-phenyl-methylidene]-5-phenylsulphonylamino-2-indolinone | 258–260 |
| | phenyl | N-methyl-N-methylsulphonyl-amino | H | (Z)-3-[1-(4-(N-methyl-N-methylsulphonyl-amino)-phenylamino)-1-phenyl-methylidene]-5-phenylsulphonylamino-2-indolinone | 306–308 |
| | phenyl | ethylsulphonylamino | H | (Z)-3-[1-(4-ethylsulphonylamino-phenylamino)-1-phenyl-methylidene]-5-phenylsulphonylamino-2-indolinone | 177–179 |
| | phenyl | N-[2-(N-acetyl-N-methyl-amino)-ethyl]-N-propionyl-amino | H | (Z)-3-{1-[4-(N-(2-(N-acetyl-N-methyl-amino)-ethyl)-N-propionyl-amino)-phenylamino]-1-phenyl-methylidene}-5-phenylsulphonylamino-2-indolinone | 250 |
| | phenyl | N-[2-(N-benzyl-N-methyl-amino)-ethyl]-N-propionyl-amino | H | (Z)-3-{1-[4-(N-(2-(N-benzyl-N-methyl-amino)-ethyl)-N-propionyl-amino)-phenylamino]-1-phenyl-methylidene}-5-phenylsulphonylamino-2-indolinone | 220 |
| | phenyl | dimethylaminocarbonylmethylamino | H | (Z)-3-{1-[4-(dimethylaminocarbonylmethylamino)-phenylamino]-1-phenyl-methylidene}-5-phenylsulphonylamino-2-indolinone | 230–231 |
| | phenyl | formylamino | H | (Z)-3-[1-(4-formylamino-phenylamino)-1-phenyl-methylidene]-5-phenylsulphonylamino-2-indolinone | 305–307 |
| | phenyl | (2,6-dimethylpiperidino)-methyl | H | (Z)-3-{1-[4-((2,6-dimethylpiperidino)-methyl)-phenylamino]-1-phenyl-methylidene}-5-phenylsulphonylamino-2-indolinone | 144–145 |
| | phenyl | N-(dimethyl-aminomethylcarbonyl)-N-methyl-amino | H | (Z)-3-{1-[4-(N-dimethylaminomethylcarbonyl-N-methyl-amino)-phenylamino]-1-phenyl-methylidene}-5-phenylsulphonylamino-2-indolinone | 242 |
| | phenyl | N-(2-dimethylamino-ethyl)-N-benzylsulphonyl-amino | H | (Z)-3-{1-[4-(N-(2-dimethylamino-ethyl)-N-benzylsulphonyl-amino)-phenylamino]-1-phenyl-methylidene}-5-phenylsulphonylamino-2-indolinone | 80 (decomp.) |
| | phenyl | 2-propionylamino-ethylamino | H | (Z)-3-{1-[4-(2-propionylamino-ethylamino)-phenylamino]-1-phenyl-methylidene}-5-phenylsulphonylamino-2-indolinone | 216 |
| | phenyl | N-tert.butoxycarbonyl-N-propyl-aminomethyl | H | (Z)-3-{1-[4-(N-tert.butoxycarbonyl-N-propyl-aminomethyl)-phenylamino]-1-phenyl-methylidene}-5-phenylsulphonylamino-2-indolinone | 215 |
| | phenyl | N-tert.butoxycarbonyl-N-butyl-aminomethyl | H | (Z)-3-{1-[4-(N-tert.butoxycarbonyl-N-butyl-aminomethyl)-phenylamino]-1-phenyl-methylidene}-5-phenylsulphonylamino-2-indolinone | 207 |
| | phenyl | methyl | H | (Z)-3-[1-(4-methyiphenylamino)-1-phenyl-methylidene]-5-phenylsulphonylamino-2-indolinone | 192 |
| | phenyl | N-methyl-N-ethyl-aminomethyl | H | (Z)-3-[1-(4-(N-methyl-N-ethyl-aminomethyl)-phenylamino)-1-phenyl-methylidene]-5-phenylsulphonylamino-2-indolinone | 256 |
| | phenyl | N-methyl-N-piperidinomethylcarbonyl-amino | H | (Z)-3-[1-(4-(N-methyl-N-piperidinomethylcarbonyl-amino)-phenylamino)-1-phenyl-methylidene]-5-phenylsulphonylamino-2-indolinone | 274–276 |
| | benzyl | dimethylaminomethyl | H | (Z)-3-{1-[4-dimethylaminomethyl-phenylamino]-1-phenyl-methylidene}-5-benzylsulphonylamino-2-indolinone | 242–243 |

TABLE I-continued

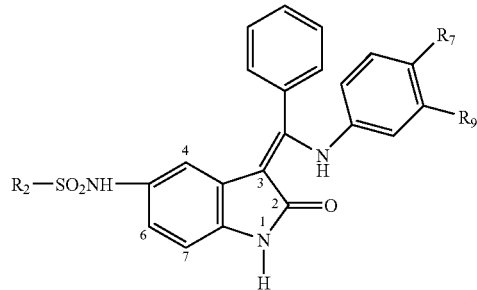

(IA)

| Example | $R_2$ | $R_7$ | $R_9$ | chemical name | Melting point (° C.) |
|---|---|---|---|---|---|
| | benzyl | pyrrolidin-1-ylmethyl | H | (Z)-3-{1-[4-(pyrrolidin-1-ylmethyl)-phenylamino]-1-phenyl-methylidene}-5-benzylsulphonylamino-2-indolinone | 228 |
| | benzyl | tert.butoxycarbonyl-aminomethyl | H | (Z)-3-[1-(4-tert.butoxycarbonylaminomethyl-phenylamino)-1-phenyl-methylidene]-5-benzylsulphonylamino-2-indolinone | 205 |
| | benzyl | (2,6-dimethylpiperidino)-methyl | H | (Z)-3-{1-[4-((2,6-dimethylpiperidino)-methyl)-phenylamino]-1-phenyl-methylidene}-5-benzylsulphonylamino-2-indolinone | 140 (decomp.) |
| | 3-methoxy-phenyl | (2,6-dimethylpiperidino)-methyl | H | (Z)-3-{1-[4-((2,6-dimethylpiperidino)-methyl)-phenylamino]-1-phenyl-methylidene}-5-(3-methoxyphenylsulphonylamino)-2-indolinone | 186 |
| | 3-methoxy-phenyl | pyrrolidin-1-ylmethyl | H | (Z)-3-{1-[4-(pyrrolidin-1-ylmethyl)-phenylamino]-1-phenyl-methylidene}-5-(3-methoxyphenylsulphonylamino)-2-indolinone | 233 |
| | 3-methoxy-phenyl | tert.butoxycarbonyl-aminomethyl | H | (Z)-3-[1-(4-tert.butoxycarbonylaminomethyl-phenylamino)-1-phenyl-methylidene]-5-(3-methoxyphenylsulphonylamino)-2-indolinone | 189 |
| | 3-nitro-phenyl | pyrrolidin-1-ylmethyl | H | (Z)-3-{1-[4-(pyrrolidin-1-ylmethyl)-phenylamino]-1-phenyl-methylidene}-5-(3-nitrophenylsulphonylamino)-2-indolinone | 181 |
| | 3-nitro-phenyl | tert.butoxycarbonyl-aminomethyl | H | (Z)-3-[1-(4-tert.butoxycarbonylaminomethyl)-phenylamino]-1-phenyl-methylidene]-5-(3-nitrophenylsulphonylamino)-2-indolinone | 238° C. (decomp.) |
| | 3-nitro-phenyl | (2,6-dimethylpiperidino)-methyl | H | (Z)-3-{1-[4-((2,6-dimethylpiperidino)-methyl)-phenylamino]-1-phenyl-methylidene}-5-(3-nitrophenylsulphonylamino)-2-indolinone | 215 |
| | 2-cyano-phenyl | 4-methylpiperazino-methyl | H | (Z)-3-{1-[4-(4-methylpiperazinomethyl)-phenylamino]-1-phenyl-methylidene}-5-(2-cyanophenylsulphonylamino)-2-indolinone | 255 (decomp.) |
| | 3-amino-carbonyl-phenyl | 4-methylpiperazino-methyl | H | (Z)-3-{1-[4-(4-methylpiperazinomethyl)-phenylamino]-1-phenyl-methylidene}-5-(3-aminocarbonyl-phenyl sulphonylamino)-2-indolinone | 278 (decomp.) |
| | ethyl | H | H | (Z)-3-(1-phenylamino-1-phenyl-methylidene)-5-ethylsulphonylamino-2-indolinone | 309 |
| | ethyl | dimethylaminomethyl | H | (Z)-3-{1-[4-dimethylaminomethyl-phenylamino]-1-phenyl-methylidene}-5-ethylsulphonylamino-2-indolinone | 230 |
| | ethyl | N-benzyl-N-methyl-aminomethyl | H | (Z)-3-{1-[4-(N-benzyl-N-methyl-aminomethyl)-phenylamino]-1-phenyl-methylidene}-5-ethylsulphonylamino-2-indolinone | 223 |
| | ethyl | 2-dimethylamino-ethyl | H | (Z)-3-{1-[4-(2-dimethylamino-ethyl)-phenylamino]-1-phenyl-methylidene}-5-ethylsulphonylamino-2-indolinone | 242 |
| | ethyl | N-(2-dimethylamino-ethyl)-N-methyl-sulphonyl-amino | H | (Z)-3-{1-[4-(N-(2-dimethylamino-ethyl)-N-methylsulphonyl-amino)-phenylamino]-1-phenyl methylidene}-5-ethylsulphonylamino-2-indolinone | 240 |
| | ethyl | Cl | H | (Z)-3-[1-(4-chlorophenylamino)-1-phenyl-methylidene]-5-ethylsulphonylamino-2-indolinone | 274 |
| | ethyl | nitro | H | (Z)-3-{1-[4-nitrophenylamino]-1-phenyl-methylidene}-5-ethylsulphonylamino-2-indolinone | 270 |
| | phenyl | N-tert.butoxycarbonyl-N-ethyl-aminomethyl | H | (Z)-3-{1-[4-(N-tert.butoxycarbonyl-N-ethyl-aminomethyl)-phenylamino]-1-phenyl-methylidene}-5-phenylsulphonylamino-2-indolinone | 225 |
| | ethyl | 4-(3-aminopropyl)-piperidinomethyl | H | (Z)-3-{1-[4-(4-(3-aminopropyl)-piperidinomethyl)-phenylamino]-1-phenyl-methylidene}-5-ethylsulphonylamino-2-indolinone | 224 |
| | ethyl | 4-(3-acetylamino-propyl)-piperidinomethyl | H | (Z)-3-{1-[4-(4-(3-acetylamino-propyl)-piperidinomethyl)-phenylamino]-1-phenyl-methylidene}-5-ethylsulphonylamino-2-indolinone | 145 |

TABLE I-continued

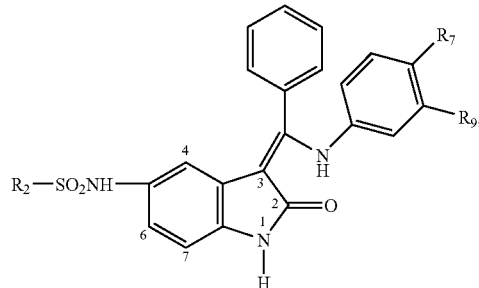

(IA)

| Example | R₂ | R₇ | R₉ | chemical name | Melting point (° C.) |
|---|---|---|---|---|---|
| | pyridin-3-yl | dimethylaminomethyl | H | (Z)-3-{1-[4-dimethylaminomethyl-phenylamino]-1-phenyl-methylidene}-5-(pyridin-3-ylsulphonylamino)-2-indolinone | 246–247 |
| | pyridin-3-yl | pyrrolidin-1-ylmethyl | H | (Z)-3-{1-[4-(pyrrolidin-1-ylmethyl)-phenylamino]-1-phenyl-methylidene}-5-(pyridin-3-ylsulphonylamino)-2-indolinone | 235–236 |
| | pyridin-3-yl | N-acetyl-N-methyl-amino | H | (Z)-3-{1-[4-(N-acetyl-N-methyl-amino)-phenylamino]-1-phenyl-methylidene}-5-(pyridin-3-ylsulphonylamino)-2-indolinone | 240–241 |
| | pyridin-3-yl | N-methyl-N-methylsulphonyl-amino | H | (Z)-3-{1-[4-(N-methyl-N-methylsulphonyl-amino)-phenylamino]-1-phenyl-methylidene}-5-(pyridin-3-ylsulphonylamino)-2-indolinone | 286–287 |
| | pyridin-3-yl | N-(2-dimethylamino-ethyl)-N-methylsulphonyl-amino | H | (Z)-3-{1-[4-(N-(2-dimethylamino-ethyl)-N-methylsulphonyl-amino)-phenylamino]-1-phenyl-methylidene}-5-(pyridin-3-ylsulphonylamino)-2-indolinone | 249–250 |
| | pyridin-3-yl | 1H-imidazol-2-yl | H | (Z)-3-{1-[4-(1H-imidazol-2-yl)-phenylamino]-1-phenyl-methylidene}-5-(pyridin-3-ylsulphonylamino)-2-indolinone | 222–223 |
| | pyridin-3-yl | 1-methyl-1H-imidazol-2-yl | H | (Z)-3-{1-[4-(1-methyl-1H-imidazol-2-yl)-phenylamino]-1-phenyl-methylidene}-5-(pyridin-3-ylsulphonylamino)-2-indolinone | 230–231 |
| | pyridin-3-yl | dimethylamino-carbonyl | H | (Z)-3-{1-[4-dimethylaminocarbonyl-phenylamino]-1-phenyl-methylidene}-5-(pyridin-3-ylsulphonylamino)-2-indolinone | 171–172 |
| | pyridin-3-yl | 4-methyl-piperazinomethyl | H | (Z)-3-{1-[4-(4-methylpiperazinomethyl)-phenylamino]-1-phenyl-methylidene}-5-(pyridin-3-ylsulphonylamino)-2-indolinone | 258–259 |
| | pyridin-3-yl | pyrrolidin-1-ylcarbonyl | H | (Z)-3-{1-[4-(pyrrolidin-1-ylcarbonyl)-phenylamino]-1-phenyl-methylidene}-5-(pyridin-3-ylsulphonylamino)-2-indolinone | 284–285 |
| | pyridin-3-yl | N-(2-dimethylamino-ethyl)-N-methylsulphonyl-amino | Cl | (Z)-3-{1-[3-chloro-4-(N-(2-dimethylamino-ethyl)-N-methylsulphonyl-amino)-phenylamino]-1-phenyl-methylidene}-5-(pyridin-3-ylsulphonylamino)-2-indolinone | 261–262 |
| | pyridin-3-yl | N-(2-dimethylamino-ethyl)-N-methylsulphonyl-amino | NH₂ | (Z)-3-{1-[3-amino-4-(N-(2-dimethylamino-ethyl)-N-methylsulphonyl-amino)-phenylamino]-1-phenyl-methylidene}-5-(pyridin-3-ylsulphonylamino)-2-indolinone | 272–273 |
| | pyridin-2-yl | 4-methyl-piperazinomethyl | H | (Z)-3-{1-[4-(4-methylpiperazinomethyl)-phenylamino]-1-phenyl-methylidene}-5-(pyridin-2-ylsulphonylamino)-2-indolinone | 210 (decomp.) |
| | pyridin-2-yl | N-acetyl-N-[2-(N-benzyl-N-methyl-amino)-ethyl]-amino | H | (Z)-3-{1-[4-(N-acetyl-N-(2-(N-benzyl-N-methyl-amino)-ethyl)-amino)-phenylamino]-1-phenyl-methylidene}-5-(pyridin-2-ylsulphonylamino)-2-indolinone | 232–235 |
| | pyridin-2-yl | N-(3-dimethylamino-propyl)-N-propionyl-amino | H | (Z)-3-{1-[4-(N-(3-dimethylamino-propyl)-N-propionyl-amino)-phenyl amino]-1-phenyl-methylidene}-5-(pyridin-2-ylsulphonylamino)-2-indolinone | 217–219 |
| | pyridin-2-yl | N-(3-dimethylamino-propyl)-N-methylsulphonyl-amino | H | (Z)-3-{1-[4-(N-(3-dimethylamino-propyl)-N-methylsulphonyl-amino)-phenylamino]-1-phenyl-methylidene}-5-(pyridin-2-ylsulphonylamino)-2-indolinone | 258–260 |
| | pyridin-2-yl | N-(3-dimethylamino-propyl)-N-propylsulphonyl-amino | H | (Z)-3-{1-[4-(N-(3-dimethylamino-propyl)-N-propylsulphonyl-amino)-phenylamino]-1-phenyl-methylidene}-5-(pyridin-2-ylsulphonylamino)-2-indolinone | 256–257 |

TABLE I-continued

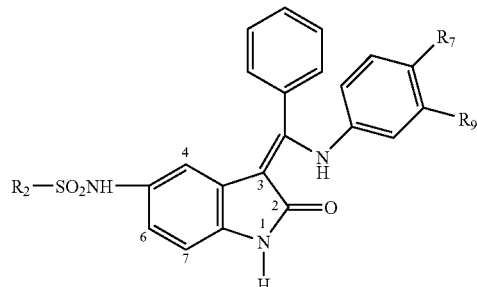

(IA)

| Example | $R_2$ | $R_7$ | $R_9$ | chemical name | Melting point (° C.) |
|---|---|---|---|---|---|
| | pyridin-2-yl | N-(2-dimethylamino-ethyl)-N-methylsulphonyl-amino] | H | (Z)-3-{1-[4-(N-(2-dimethylamino-ethyl)-N-methylsulphonyl-amino)-phenylamino]-1-phenyl-methylidene}-5-(pyridin-2-ylsulphonylamino)-2-indolinone | 269–271 |
| | pyridin-2-yl | N-piperidinomethyl-carbonyl-N-methyl-amino | H | (Z)-3-{1-[4-(N-piperidinomethylcarbonyl-N-methyl-amino)-phenylamino]-1-phenyl-methylidene}-5-(pyridin-2-ylsulphonylamino)-2-indolinone | 236–237 |

EXAMPLE 98

(Z)-3-[1-(4-piperidinomethyl-phenylamino)-1-phenyl-methylidene]-5-methylsulphonylamino-2-indolinone a. 1-acetyl-3-(1-ethoxy-1-phenyl-methylidene)-5-nitro-2-indolinone 0.2 g (0.9 mmol) of 1-acetyl-5-nitro-2-indolinone and 0.6 g (2.7 mmol) of triethyl orthobenzoate are heated to 100° C. in 2 ml of acetic acid anhydride for 1.5 hours. After cooling the mixture is combined with ether and the precipitate formed is suction filtered.

Yield: 0.2 g (66% of theory), Melting point: 244–250° C. $R_f$ value: 0.7 (silica gel; ethyl acetate/cyclohexane=3:2)

b. (Z)-1-acetyl-3-[1-(4-piperidinomethyl-phenylamino)-1-phenyl-methylidene]-5-nitro-2-indolinone 3 g (8.5 mmol) of 1-acetyl-3-(1-ethoxy-1-phenyl-methylidene)-5-nitro-2-indolinone and 1.9 g (10 mmol) of 4-piperidinomethyl-aniline are heated to 90° C. in 30 ml of DMF for 3.5 hours. After cooling to ambient temperature the reaction solution is poured onto ice water and extracted with ethyl acetate. The combined organic extracts are dried and evaporated down. The residue is triturated with ether and suction filtered.

Yield: 3.5 g (82% of theory), $R_f$ value: 0.6 (silica gel; dichloromethane/methanol/ammonia=9:1:0.1) Melting point: 165° C.

c. (Z)-1-acetyl-3-[1-(4-piperidinomethyl-phenylamino)-1-phenyl-methylidene]-5-amino-2-indolinone Prepared analogously to Example VIIb from (Z)-1-acetyl-3-[1-(4-piperidinomethyl-phenylamino)-1-phenyl-methylidene]-5-nitro-2-indolinone by catalytic reduction over Raney nickel in dichloromethane/methanol (1:1).

Yield: 99% of theory, $R_f$ value: 0.5 (silica gel; dichloromethane/methanol/ammonia=9:1:0.1) Melting point: 278–281° C. $C_{29}H_{30}N_4O_2$ (466.59) Mass spectrum: $(M+H)^+=467$ d. (Z)-3-[1-(4-piperidinomethyl-phenylamino)-1-phenyl-methylidene]-5-methylsulphonylamino-2-indolinone 466 mg (1 mmol) of (Z)-1-acetyl-3-[1-(4-piperidinomethyl-phenylamino)-1-phenyl-methylidene]-5-amino-2-indolinone are suspended in 15 ml of pyridine, combined with 0.2 ml (2.3 mmol) of methanesulphonic acid chloride and stirred for 1.5 hours. Then 6 ml of 1 N sodium hydroxide solution are added. After 1 hour 1 ml of piperidine is added and the mixture is stirred overnight. The reaction solution is poured onto water and the precipitate formed is suction filtered. The residue is stirred with ether, suction filtered and dried.

Yield: 290 mg (58% of theory), $R_f$ value: 0.4 (silica gel; dichloromethane/methanol/ammonia=9:1:0.1) Melting point: 266° C. $C_{28}H_{30}N_4O_3S$ (502.64) Mass spectrum: $(M+H)^+=503$

| | | | |
|---|---|---|---|
| Calc.: | C 66.91 | H 6.02 | N 11.15 |
| Found: | C 66.49 | H 6.06 | N 11.01 |

EXAMPLES 99 TO 151

Using the intermediate products prepared in Examples I to XIII, the compounds of formula IB of Examples 99 to 151 listed in Table II are prepared analogously to Example 98.

Hydrochlorides or dihydrochlorides are obtained according to the following general working method: The starting compound is dissolved in dichloromethane and combined with ether/HCl. The precipitate formed is suction filtered and dried.

TABLE II

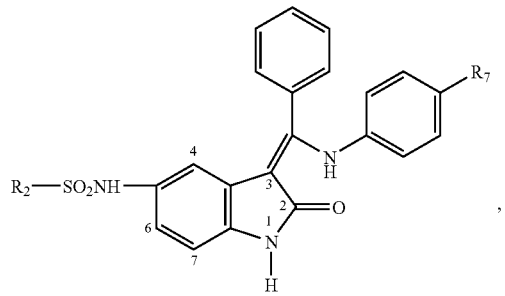

(IB)

| Example | R₂ | R₇ | chemical name | Melting point (° C.) |
|---|---|---|---|---|
| | ethyl | piperidinomethyl | (Z)-3-{1-[4-(piperidinomethyl)-phenylamino]-1-phenyl-methylidene}-5-ethylsulphonylamino-2-indolinone | 235 |
| | ethyl | methoxy | (Z)-3-[1-(4-methoxyphenylamino)-1-phenyl-methylidene]-5-ethyl-sulphonylamino-2-indolinone | 283 |
| | isopropyl | piperidinomethyl | (Z)-3-{1-[4-(piperidinomethyl)-phenylamino]-1-phenyl-methylidene}-5-isopropylsulphonylamino-2-indolinone | 205 |
| | 4-chlorophenyl | piperidinomethyl | (Z)-3-{1-[4-(piperidinomethyl)-phenylamino]-1-phenyl-methylidene}-5-(4-chlorophenylsulphonylamino)-2-indolinone | 251–253 |
| | 3-chlorophenyl | piperidinomethyl | (Z)-3-{1-[4-(piperidinomethyl)-phenylamino]-1-phenyl-methylidene}-5-(3-chlorophenylsulphonylamino)-2-indolinone | 275–277 |
| | naphthalin-1-yl | piperidinomethyl | (Z)-3-{1-[4-(piperidinomethyl)-phenylamino]-1-phenyl-methylidene}-5-(naphthalin-1-ylsulphonylamino)-2-indolinone | 236–237 |
| | 4-methylphenyl | piperidinomethyl | (Z)-3-{1-[4-(piperidinomethyl)-phenylamino]-1-phenyl-methylidene}-5-(4-methylphenylsulphonylamino)-2-indolinone | 267–269 |
| | 3-methylphenyl | piperidinomethyl | (Z)-3-{1-[4-(piperidinomethyl)-phenylamino]-1-phenyl-methylidene}-5-(3-methylphenylsulphonylamino)-2-indolinone | 269–271 |
| | 3-methoxyphenyl | piperidinomethyl | (Z)-3-{1-[4-(piperidinomethyl)-phenylamino]-1-phenyl-methylidene}-5-(3-methoxyphenylsulphonylamino)-2-indolinone | 241–245 |
| | 4-methoxyphenyl | piperidinomethyl | (Z)-3-{1-[4-(piperidinomethyl)-phenylamino]-1-phenyl-methylidene}-5-(4-methoxyphenylsulphonylamino)-2-indolinone | 253–256 |
| | 2,4,6-trimethylphenyl | piperidinomethyl | (Z)-3-{1-[4-(piperidinomethyl)-phenylamino]-1-phenyl-methylidene}-5-(2,4,6-trimethylphenylsulphonylamino)-2-indolinone | 224 |
| | 4-nitrophenyl | piperidinomethyl | (Z)-3-{1-[4-(piperidinomethyl)-phenylamino]-1-phenyl-methylidene}-5-(4-nitrophenylsulphonylamino)-2-indolinone | 276 |
| | naphthalin-2-yl | piperidinomethyl | (Z)-3-{1-[4-(piperidinomethyl)-phenylamino]-1-phenyl-methylidene}-5-(naphthalin-2-ylsulphonylamino)-2-indolinone | 234 |
| | 3-nitrophenyl | piperidinomethyl | (Z)-3-{1-[4-(piperidinomethyl)-phenylamino]-1-phenyl-methylidene}-5-(3-nitrophenylsulphonylamino)-2-indolinone | 145 |
| | quinolin-8-yl | piperidinomethyl | (Z)-3-{1-[4-(piperidinomethyl)-phenylamino]-1-phenyl-methylidene}-5-(quinolin-8-ylsulphonylamino)-2-indolinone | 279 |
| | 2-chlorophenyl | piperidinomethyl | (Z)-3-{1-[4-(piperidinomethyl)-phenylamino]-1-phenyl-methylidene}-5-(2-chlorophenylsulphonylamino)-2-indolinone | 275 |
| | 2-nitrophenyl | piperidinomethyl | (Z)-3-{1-[4-(piperidinomethyl)-phenylamino]-1-phenyl-methylidene}-5-(2-nitrophenylsulphonylamino)-2-indolinone | 140 |
| | 3-cyanophenyl | piperidinomethyl | (Z)-3-{1-[4-(piperidinomethyl)-phenylamino]-1-phenyl-methylidene}-5-(3-cyanophenylsulphonylamino)-2-indolinone | 248 |
| | 3,5-dimethylisoxazol-4-yl | piperidinomethyl | (Z)-3-{1-[4-(piperidinomethyl)-phenylamino]-1-phenyl-methylidene}-5-(3,5-dimethylisoxazol-4-ylsulphonylamino)-2-indolinone | 240 |
| | E-2-phenylethenyl | piperidinomethyl | (Z)-3-{1-[4-(piperidinomethyl)-phenylamino]-1-phenyl-methylidene}-5-((E)-2-phenylethenylsulphonylamino)-2-indolinone | 248 |
| | 1-methyl-1H-imidazol-4-yl | piperidinomethyl | (Z)-3-{1-[4-(piperidinomethyl)-phenylamino]-1-phenyl-methylidene}-5-(1-methyl-1H-imidazol-4-ylsulphonylamino)-2-indolinone-dihydrochloride | 230 |
| | cyclopropyl | piperidinomethyl | (Z)-3-{1-[4-(piperidinomethyl)-phenylamino]-1-phenyl-methylidene}-5-cyclopropylsulphonylamino-2-indolinone | 231 |
| | 2-cyanophenyl | piperidinomethyl | (Z)-3-{1-[4-(piperidinomethyl)-phenylamino]-1-phenyl-methylidene}-5-(2-cyanophenylsulphonylamino)-2-indolinone | 239 |
| | pyridin-2-yl | piperidinomethyl | (Z)-3-{1-[4-(piperidinomethyl)-phenylamino]-1-phenyl-methylidene}-5-(pyridin-2-ylsulphonylamino)-2-indolinone | 263 |
| | phenyl | piperidinomethyl | (Z)-3-{1-[4-(piperidinomethyl)-phenylamino]-1-phenyl-methylidene}-5-phenylsulphonylamino-2-indolinone | 262 |
| | benzyl | piperidinomethyl | (Z)-3-{1-[4-(piperidinomethyl)-phenylamino]-1-phenyl-methylidene}-5-benzylsulphonylamino-2-indolinone | 254 |
| | propyl | piperidinomethyl | (Z)-3-{1-[4-(piperidinomethyl)-phenylamino]-1-phenyl-methylidene}-5-propylsulphonylamino-2-indolinone | 188 |

TABLE II-continued (IB)

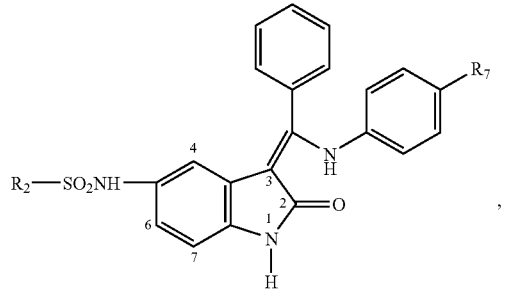

| Example | R₂ | R₇ | chemical name | Melting point (° C.) |
|---|---|---|---|---|
| | benzyl | N-(2-dimethylamino-ethyl)-N-methyl-sulphonyl-amino | (Z)-3-{1-[4-(N-(2-dimethylamino-ethyl)-N-methylsulphonyl-amino)-phenylamino]-1-phenyl-methylidene}-5-benzylsulphonylamino-2-indolinone | 163–164 |
| | isopropyl | 2-dimethylamino-ethyl | (Z)-3-{1-[4-(2-dimethylamino-ethyl)-phenylamino]-1-phenyl-methylidene}-5-isopropylsulphonylamino-2-indolinone | 220 |
| | propyl | 2-dimethylamino-ethyl | (Z)-3-{1-[4-(2-dimethylamino-ethyl)-phenylamino]-1-phenyl-methylidene}-5-propylsulphonylamino-2-indolinone | 239–240 |
| | propyl | N-benzyl-N-methyl-aminomethyl | (Z)-3-{1-[4-(N-benzyl-N-methyl-aminomethyl)-phenylamino]-1-phenyl-methylidene}-5-propylsulphonylamino-2-indolinone | 195–197 |
| | methyl | N-benzyl-N-methyl-aminomethyl | (Z)-3-{1-[4-(N-benzyl-N-methyl-aminomethyl)-phenylamino]-1-phenyl-methylidene}-5-methylsulphonylamino-2-indolinone | 241–242 |
| | phenyl | N-benzyl-N-methyl-aminomethyl | (Z)-3-{1-[4-(N-benzyl-N-methyl-aminomethyl)-phenylamino]-1-phenyl-methylidene}-5-phenylsulphonylamino-2-indolinone | 148–150 |
| | benzyl | N-benzyl-N-methyl-aminomethyl | (Z)-3-{1-[4-(N-benzyl-N-methyl-aminomethyl)-phenylamino]-1-phenyl-methylidene}-5-benzylsulphonylamino-2-indolinone | 200–204 |
| | benzyl | 2-dimethylamino-ethyl | (Z)-3-{1-[4-(2-dimethylamino-ethyl)-phenylamino]-1-phenyl-methylidene}-5-benzylsulphonylamino-2-indolinone-hydrochloride | 260–262 |
| | pyridin-3-yl | piperidinomethyl | (Z)-3-{1-[4-(piperidinomethyl)-phenylamino]-1-phenyl-methylidene}-5-(pyridin-3-ylphenylsulphonylamino)-2-indolinone | 236 |
| | 3-nitrophenyl | dimethylamino-methyl | (Z)-3-{1-[4-(dimethylaminomethyl)-phenylamino]-1-phenyl-methylidene}-5-(3-nitrophenylsulphonylamino)-2-indolinone | 246–247 |
| | 3-methoxy-phenyl | dimethylamino-methyl | (Z)-3-{1-[4-(dimethylaminomethyl)-phenylamino]-1-phenyl-methylidene}-5-(3-methoxyphenylsulphonylamino)-2-indolinone | 259–260 |
| | 3-nitrophenyl | dimethylamino-methyl amino | (Z)-3-{1-[4-(N-methyl-N-acetyl-amino)-phenylamino]-1-phenyl-methylidene}-5-(3-nitrophenylsulphonylamino)-2-indolinone | 298–300 |
| | 2-nitrophenyl | N-methyl-N-acetyl-amino | (Z)-3-{1-[4-(N-methyl-N-acetyl-amino)-phenylamino]-1-phenyl-methylidene}-5-(2-nitrophenylsulphonylamino)-2-indolinone | 295–297 |
| | 3-cyanophenyl | N-methyl-N-acetyl-amino | (Z)-3-{1-[4-(N-methyl-N-acetyl-amino)-phenylamino]-1-phenyl-methylidene}-5-(3-cyanophenylsulphonylamino)-2-indolinone | 330–332 |
| | 3-nitrophenyl | 4-methyl-piperazinomethyl | (Z)-3-{1-[4-(4-methylpiperazinomethyl)-phenylamino]-1-phenyl-methylidene}-5-(3-nitrophenylsulphonylamino)-2-indolinone | 166–167 |
| | pyridin-2-yl | pyrrolidin-1-ylmethyl | (Z)-3-{1-[4-(pyrrolidin-1-ylmethyl)-phenylamino]-1-phenyl-methylidene}-5-(pyridin-2-ylsulphonylamino)-2-indolinone | 261 |
| | cyclopropyl | pyrrolidin-1-ylmethyl | (Z)-3-{1-[4-(pyrrolidin-1-ylmethyl)-phenylamino]-1-phenyl-methylidene}-5-cyclopropylsulphonylamino-2-indolinone | 256 |
| | propyl | pyrrolidin-1-ylmethyl | (Z)-3-{1-[4-(pyrrolidin-1-ylmethyl)-phenylamino]-1-phenyl-methylidene}-5-propylsulphonylamino-2-indolinone | 247 |
| | ethyl | pyrrolidin-1-ylmethyl | (Z)-3-{1-[4-(pyrrolidin-1-ylmethyl)-phenylamino]-1-phenyl-methylidene}-5-ethylsulphonylamino-2-indolinone | 245 |
| | methyl | pyrrolidin-1-ylmethyl | (Z)-3-{1-[4-(pyrrolidin-1-ylmethyl)-phenylamino]-1-phenyl-methylidene}-5-methylsulphonylamino-2-indolinone | 248 |
| | 2-fluorophenyl | pyrrolidin-1-ylmethyl | (Z)-3-{1-[4-(pyrrolidin-1-ylmethyl)-phenylamino]-1-phenyl-methylidene}-5-(2-fluorophenylsulphonylamino)-2-indolinone | 247 |
| | 4-fluorophenyl | pyrrolidin-1-ylmethyl | (Z)-3-{1-[4-(pyrrolidin-1-ylmethyl)-phenylamino]-1-phenyl-methylidene}-5-(4-fluorophenylsulphonylamino)-2-indolinone | 244 |
| | 3-fluorophenyl | pyrrolidin-1-ylmethyl | (Z)-3-{1-[4-(pyrrolidin-1-ylmethyl)-phenylamino]-1-phenyl-methylidene}-5-(3-fluorophenylsulphonylamino)-2-indolinone | 257 |
| | 2-nitrophenyl | pyrrolidin-1-ylmethyl | (Z)-3-{1-[4-(pyrrolidin-1-ylmethyl)-phenylamino]-1-phenyl-methylidene}-5-(2-nitrophenylsulphonylamino)-2-indolinone | 185 |
| | 3-cyanophenyl | pyrrolidin-1-ylmethyl | (Z)-3-{1-[4-(pyrrolidin-1-ylmethyl)-phenylamino]-1-phenyl-methylidene}-5-(3-cyanophenylsulphonylamino)-2-indolinone | 249 |
| | 2-cyanophenyl | pyrrolidin-1-ylmethyl | (Z)-3-{1-[4-(pyrrolidin-1-ylmethyl)-phenylamino]-1-phenyl-methylidene}-5-(2-cyanophenylsulphonylamino)-2-indolinone | 232 |

EXAMPLE 152

(Z)-3-[1-(4-ethoxycarbonylmethyl-phenylamino)-1-phenyl-methylidene]-5-phenylsulphonylamino-2-indolinone a. 3-(1-ethoxy-1-phenyl-methylidene)-5-phenylsulphonylamino-2-indolinone 8 ml of 4 N sodium hydroxide solution are added to a solution of 4.0 g (8 mmol) of 1-acetyl-3-(1-ethoxy-1-phenyl-methylidene)-5-(N-acetyl-N-phenylsulphonyl-amino)-2-indolinone (Example 1e) in a mixture of 20 ml of dichloromethane and 20 ml of ethanol and the resulting mixture is stirred for 20 minutes at ambient temperature. It is then evaporated down to about. 10 ml and 150 ml of water are added. The pH is adjusted to 8–9 with 1 N hydrochloric acid. The precipitate formed is suction filtered, washed with water, isopropanol and ether, then dried in vacuo.

Yield: 6.6 g (82% of theory), Melting point: 292–294° C. $R_f$ value:0.4 (silica gel; dichloromethane/methanol/$NH_4OH$=9:1:0.1) $C_{23}H_{20}N_2O_4S$ (420.49) Mass spectrum: $(M+H)^+$=421, $(M-H)^-$=419 b. (Z)-3-[1-(4-ethoxycarbonylmethyl-phenylamino)-1-phenyl-methylidene]-5-phenylsulphonylamino-2-indolinone 0.84 g (2 mmol) of 3-(1-ethoxy-1-phenyl-methylidene)-5-phenylsulphonylamino-2-indolinone and 0.39 g (2.2 mmol) of 4-ethoxycarbonylmethyl-aniline are dissolved in 10 ml of DMF. The mixture is heated to 140° C. for 5 hours. Then water is added while the mixture is cooled with ice and stirred for 1 hour at ambient temperature. The precipitate formed is suction filtered, washed with water, a little isopropanol and ether, then dried in vacuo.

Yield: 0.95 g (86% of theory), Melting point: 248–249° C. $C_{31}H_{27}N_3O_5S$ (553.64) Mass spectrum: $M^+$=553, $(M-H)^-$=552

EXAMPLE 153

(Z)-3-[1-(4-carboxymethyl-phenylamino)-1-phenyl-methylidene]-5-phenylsulphonylamino-2-indolinone 720 mg (1.3 mmol) of (Z)-3-[1-(4-ethoxycarbonylmethyl-phenylamino)-1-phenyl-methylidene]-5-phenylsulphonylamino-2-indolinone are dissolved in a mixture of 20 ml of methanol and 20 ml of dichloromethane. 4 ml of 1 N sodium hydroxide solution are added and the mixture is stirred for 18 hours at ambient temperature and for another 1 hour at 40° C. The reaction solution is evaporated down to half the volume and the pH is adjusted to 4–5 with 1 N hydrochloric acid. The precipitate formed is suction filtered, washed with water, a little isopropanol and ether.

Yield: 620 mg (91% of theory), Melting point: 305–306° C. $C_{29}H_{23}N_3O_5S$ (525.59) Mass spectrum: $(M-H)^-$=524

EXAMPLE 154

(Z)-3-{1-[4-(benzylaminocarbonylmethyl)-phenylamino]-1-phenyl-methylidene}-5-phenylsulphonylamino-2-indolinone A solution of 315 mg (0.6 mmol) of (Z)-3-[1-(4-carboxymethyl-phenylamino)-1-phenyl-methylidene]-5-phenylsulphonylamino-2-indolinone, 85 mg (0.8 mmol) of benzylamine, 212 mg (0.66 mmol) of TBTU and 1 ml of N-ethyl-N,N-diisopropyl-amine in 5 ml of DMF is stirred for 3 hours at ambient temperature. Then 50 ml of water are added. The yellow precipitate formed is suction filtered, washed with water, a little isopropanol and ether, then dried in vacuo.

Yield: 0.3 mg (81% of theory), Melting point: 219–220° C. $C_{36}H_{30}N_4O_4S$ (614.73) Mass spectrum: $(M+Na)^+$=637, $(M-H)^-$=613

EXAMPLE 155

(Z)-3-{1-[4-(N-(aminocarbonylmethyl)-N-methylsulphonyl-amino)-phenylamino]-1-phenyl-methylidene}-5-phenylsulphonylamino-2-indolinone A solution of 250 mg (0.4 mmol) of (Z)-3-[1-(4-(N-carboxymethyl-N-methylsulphonyl-amino)-phenylamino)-1-phenyl-methylidene]-5-phenylsulphonylamino-2-indolinone and 82 mg (0.4 mmol) of CDI in 5 ml of DMF is stirred for 1 hour at 50° C. 1 ml of condensed ammonia is added and the mixture is stirred for 5 hours at ambient temperature. Then water is added. The yellow precipitate is suction filtered, washed with water, a little isopropanol and ether, then dried in vacuo.

Yield: 190 mg (76% of theory) Melting point: 216–217° C. $C_{30}H_{27}N_5O_6S_2$ (617.71) Mass spectrum: $(M+Na)^+$=640, $(M-H)^-$=616

EXAMPLES 156 TO 170

Using the intermediate products prepared in Examples I to XIII, the compounds of formula IB of Examples 156 to 170 listed in Table III are prepared analogously to Examples 152 to 155.

TABLE III

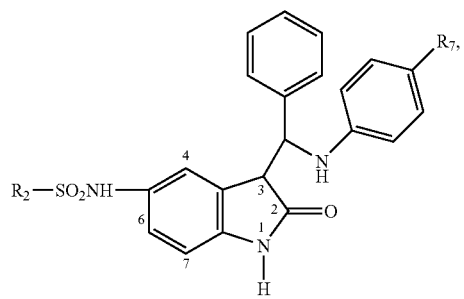

(IB)

| Example | $R_2$ | $R_7$ | chemical name | Melting point (° C.) |
|---|---|---|---|---|
| | phenyl | methoxycarbonyl | (Z)-3-[1-(4-methoxycarbonyl-phenylamino)-1-phenyl-methylidene]-5-phenylsulphonylamino-2-indolinone | 304–305 |

TABLE III-continued (IB)

| Example | R$_2$ | R$_7$ | chemical name | Melting point (° C.) |
|---|---|---|---|---|
|  | phenyl | carboxy | (Z)-3-[1-(4-carboxyphenylamino)-1-phenyl-methylidene]-5-phenylsulphonylamino-2-indolinone | 312–313 |
|  | phenyl | benzylaminocarbonyl | (Z)-3-{1-[4-(benzylaminocarbonyl)-phenylamino]-1-phenyl-methylidene}-5-phenylsulphonylamino-2-indolinone | 269–270 |
|  | methyl | methoxycarbonyl | (Z)-3-[1-(4-methoxycarbonyl-phenylamino)-1-phenyl-methylidene]-5-methylsulphonylamino-2-indolinone | >270 |
|  | methyl | carboxy | (Z)-3-[1-(4-carboxyphenylamino)-1-phenyl-methylidene]-5-methylsulphonylamino-2-indolinone | >270 |
|  | phenyl | N-carboxymethyl-N-acetyl-amino | (Z)-3-{1-[4-(N-carboxymethyl-N-acetyl-amino)-phenylamino]-1-phenyl-methylidene}-5-phenylsulphonylamino-2-indolinone | 190–191 |
|  | phenyl | N-aminocarbonylmethyl-N-acetyl-amino | (Z)-3-{1-[4-(N-(aminocarbonylmethyl)-N-acetyl-amino)-phenylamino]-1-phenyl-methylidene}-5-phenylsulphonylamino-2-indolinone | 150 (decomp.) |
|  | phenyl | N-methylaminocarbonyl-methyl-N-acetyl-amino | (Z)-3-{1-[4-(N-methylaminocarbonylmethyl-N-acetyl-amino)-phenylamino]-1-phenyl-methylidene}-5-phenylsulphonylamino-2-indolinone | 150 (decomp.) |
|  | phenyl | N-dimethylaminocarbonyl-methyl)-N-acetyl-amino) | (Z)-3-{1-[4-(N-dimethylaminocarbonylmethyl-N-acetyl-amino)-phenylamino]-1-phenyl-methylidene}-5-phenylsulphonylamino-2-indolinone | 150 (decomp.) |
|  | phenyl | N-carboxymethyl-N-ethylsulphonyl-amino | (Z)-3-{1-[4-(N-carboxymethyl-N-ethylsulphonyl-amino)-phenylamino]-1-phenyl-methylidene}-5-phenylsulphonylamino-2-indolinone | 231–235 |
|  | phenyl | N-[N-(2-dimethylamino-ethyl)-N-methyl-amino-carbonylmethyl]-N-ethylsulphonyl-amino | (Z)-3-{1-[4-(N-(N-(2-dimethylamino-ethyl)-N-methyl-aminocarbonylmethyl)-N-ethylsulphonyl-amino)-phenylamino]-1-phenyl-methylidene}-5-phenylsulphonylamino-2-indolinone | 147–151 |
|  | phenyl | N-[(2-dimethylamino-ethyl)-aminocarbonylmethyl]-N-ethylsulphonyl-amino | (Z)-3-{1-[4-(N-((2-dimethylamino-ethyl)-aminocarbonylmethyl)-N-ethylsulphonyl-amino)-phenylamino]-1-phenyl-methylidene}-5-phenylsulphonylamino-2-indolinone | 142–147 |
|  | phenyl | N-carboxylmethyl-N-methylsulphonyl-amino | (Z)-3-{1-[4-(N-carboxylmethyl-N-methylsulphonyl-amino)-phenylamino]-1-phenyl-methylidene}-5-phenylsulphonylamino-2-indolinone | 215–216 |
|  | phenyl | N-methylaminocarbonyl-methyl-N-methylsulphonyl-amino | (Z)-3-{1-[4-(N-methylaminocarbonylmethyl-N-methylsulphonyl-amino)-phenylamino]-1-phenyl-methylidene}-5-phenylsulphonylamino-2-indolinone | 150 (decomp.) |
|  | phenyl | N-dimethylamino-carbonylmethyl-N-methylsulphonyl-amino | (Z)-3-{1-[4-(N-dimethylaminocarbonylmethyl-N-methylsulphonyl-amino)-phenylamino]-1-phenyl-methylidene}-5-phenylsulphonylamino-2-indolinone | 150 (decomp.) |

EXAMPLES 171 TO 206

The compounds of formula IB of Examples 171 to 206 listed in the following Table IV are obtained from compounds of the abovementioned Examples 1 to 170 by the following general methods A to E or analogously to Example 1 or 210:

A: Cleaving of tert.butoxycarbonyl:

0.6 mmol of the starting compound are dissolved in 5 ml of dichloromethane. 10 ml of ethyl acetate/HCl are added and the mixture is stirred for 2 hours at ambient temperature. Then a basic pH is obtained by the addition of sodium hydroxide solution. The organic phase is washed with water, dried over sodium sulphate and the solvent is eliminated in vacuo. In order to prepare hydrochlorides the addition of sodium hydroxide solution is omitted. In order to prepare hydrotrifluoroacetate, trifluoroacetic acid is added to the solution of the starting compound.

B: Cleaving of Benzyl:

1.5 mmol of the starting compound are dissolved in 20 ml of dichloromethane/methanol (1:1). 100 mg of palladium/charcoal (10%) and 1.5 ml of 1 N hydrochloric acid are added and the mixture is then hydrogenated in a hydrogen atmosphere at 50 psi. The catalyst is suction filtered and the filtrate is evaporated to dryness. The residue is chromatographed on silica gel (dichloromethane/methanol/NH$_4$OH, 9:1:0.1).

C: Hydrogenation of Cyano to CH$_2$NH$_2$:

0.5 mmol of the starting compound are dissolved in 20 ml of methanolic ammonia solution and combined with Raney nickel. The mixture is hydrogenated in a hydrogen atmosphere of 50 psi, then the catalyst is suction filtered and the solvent is eliminated in vacuo. The residue is chromatographed on silica gel (dichloromethane/methanol/NH$_4$OH, 9:1:0.1).

D: Hydrogenation of Nitro to Amino:

0.2 mmol of the starting compound are dissolved in 20 ml of ethyl acetate/methanol (1:1). Then the mixture is hydrogenated analogously to Method C over Raney nickel. The residue is optionally chromatographed on silica gel (dichloromethane/methanol/NH$_4$OH, 9:1:0.1).

TABLE IV

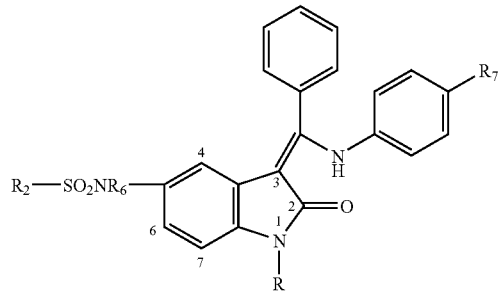

(IB),

| Example | method | R$_2$ | R$_6$ | R$_7$ | chemical name | Melting point (° C.) |
|---|---|---|---|---|---|---|
| | A | phenyl | H | amino | (Z)-3-[1-(4-aminophenylamino)-1-phenyl-methyllidene]-5-phenylsulphonylamino-2-indolinone | 220–223 |
| | A | phenyl | H | piperazino-methyl | (Z)-3-[1-(4-piperazinomethyl-phenylamino)-1-phenyl-methylidene]-5-phenylsulphonylamino-2-indolinone | 380 (decomp.) |
| | A | 3-methoxy-phenyl | H | aminomethyl | (Z)-3-[1-(4-aminomethyl-phenylamino)-1-phenyl-methylidene]-5-(3-methoxyphenylsulphonylamino)-2-indolinone-hydrochloride | 200 (decomp.) |
| | A | benzyl | H | aminomethyl | (Z)-3-[1-(4-aminomethyl-phenylamino)-1-phenyl-methylidene]-5-benzylsulphonylamino-2-indolinone-hydrochloride | 200 (decomp.) |
| | A | 3-nitrophenyl | H | aminomethyl | (Z)-3-[1-(4-aminomethyl-phenylamino)-1-phenyl-methylidene]-5-(3-nitrophenylsulphonylamino)-2-indolinone-hydrochloride | 215 (decomp.) |
| | A | phenyl | H | ethylamino-methyl | (Z)-3-[1-(4-ethylaminomethyl-phenylamino)-1-phenyl-methylidene]-5-phenylsulphonylamino-2-indolinone-hydrotrifluoroacetate | 230 |
| | A | phenyl | H | propylamino-methyl | (Z)-3-[1-(4-propylaminomethyl-phenylamino)-1-phenyl-methylidene]-5-phenylsulphonylamino-2-indolinone-hydrotrifluoroacetate | 238 |
| | A | phenyl | H | butylamino-methyl | (Z)-3-[1-(4-butylaminomethyl-phenylamino)-1-phenyl-methylidene]-5-phenylsulphonylamino-2-indolinone-hydrotrifluoroacetate | 260 |
| | B | phenyl | H | N-(2-methylamino-ethyl)-N-acetyl-amino | (Z)-3-{1-[4-(N-(2-methylamino-ethyl)-N-acetyl-amino)-phenylamino]-1-phenyl-methylidene}-5-phenylsulphonylamino-2-indolinone | 180 (decomp.) |
| | B | phenyl | H | N-(2-methylamino-ethyl)-N-propionyl-amino | (Z)-3-{1-[4-(N-(2-methylamino-ethyl)-N-propionyl-amino)-phenylamino]-1-phenyl-methylidene}-5-phenylsulphonylamino-2-indolinone | 214 |
| | C | 3-aminomethyl phenyl | H | piperidino-methyl | (Z)-3-[1-(4-piperidinomethyl-phenylamino)-1-phenyl-methylidene]-5-(3-aminomethyl-phenylsulphonylamino)-2-indolinone | 237 |
| | C | phenyl | H | aminomethyl | (Z)-3-[1-(4-aminomethyl-phenylamino)-1-phenyl-methylidene]-5-phenylsulphonylamino-2-indolinone | 230–232 |
| | C | 2-aminomethyl phenyl | H | piperidino-methyl | (Z)-3-[1-(4-piperidinomethyl-phenylamino)-1-phenyl-methylidene]-5-(2-aminomethyl-phenylsulphonylamino)-2-indolinone | 237 |
| | C | 3-aminomethyl phenyl | H | N-methyl-N-acetyl-amino | (Z)-3-{1-[4-(N-methyl-N-acetyl-amino)-phenylamino]-1-phenyl-methylidene}-5-(3-aminomethyl-phenylsulphonyl-amino)-2-indolinone | 277–279 |
| | C | 3-aminomethyl phenyl | H | pyrrolidin-1-ylmethyl | (Z)-3-[1-(4-pyrrolidin-1-ylmethyl-phenylamino)-1-phenyl-methylidene]-5-(3-aminomethyl-phenylsulphonylamino)-2-indolinone | 261 |
| | D | 4-aminophenyl | H | piperidino-methyl | (Z)-3-[1-(4-piperidinomethyl-phenylamino)-1-phenyl-methylidene]-5-(4-aminophenylsulphonylamino)-2-indolinone | 279 |

TABLE IV-continued

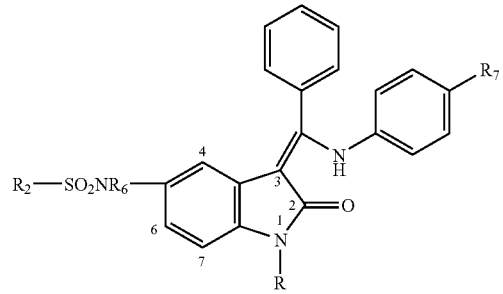

(IB),

| Example | method | R₂ | R₆ | R₇ | chemical name | Melting point (° C.) |
|---|---|---|---|---|---|---|
| | D | 3-aminophenyl | H | piperidinomethyl | (Z)-3-[1-(4-piperidinomethyl-phenylamino)-1-phenyl-methylidene]-5-(3-aminophenylsulphonylamino)-2-indolinone | 240 |
| | D | 2-aminophenyl | H | piperidinomethyl | (Z)-3-[1-(4-piperidinomethyl-phenylamino)-1-phenyl-methylidene]-5-(2-aminophenylsulphonylamino)-2-indolinone-hydrochloride | 220 (decomp.) |
| | D | 3-aminophenyl | H | dimethylaminomethyl | (Z)-3-[1-(4-dimethylaminomethyl-phenylamino)-1-phenyl-methylidene]-5-(3-aminophenylsulphonylamino)-2-indolinone | 250 (decomp.) |
| | D | 3-aminophenyl | H | N-methyl-N-acetyl-amino | (Z)-3-{1-[4-(N-methyl-N-acetyl-amino)-phenylamino]-1-phenyl-methylidene}-5-(3-aminophenylsulphonylamino)-2-indolinone | 207–209 |
| | D | 2-aminophenyl | H | N-methyl-N-acetyl-amino | (Z)-3-{1-[4-(N-methyl-N-acetyl-amino)-phenylamino]-1-phenyl-methylidene}-5-(2-aminophenylsulphonylamino)-2-indoline | 295–298 |
| | D | 3-aminophenyl | H | pyrrolidin-1-ylmethyl | (Z)-3-{1-[4-(pyrrolidin-1-ylmethyl)-phenylamino]-1-phenyl-methylidene}-5-(3-aminophenylsulphonylamino)-2-indolinone | 242 |
| | D | 3-aminophenyl | H | (2,6-dimethyl-piperidino)-methyl | (Z)-3-{1-[4-((2,6-dimethylpiperidino)-methyl)-phenylamino]-1-phenyl-methylidene}-5-(3-aminophenyl-sulphonylamino)-2-indolinone | 150 (decomp.) |
| | D | 3-aminophenyl | H | aminomethyl | (Z)-3-[1-(4-aminomethyl-phenylamino)-1-phenyl-methylidene]-5-(3-aminophenylsulphonylamino)-2-indolinone | 257 |
| | D | 3-aminophenyl | H | 4-methylpiperazinomethyl | (Z)-3-{1-[4-(4-methylpiperazinomethyl)-phenylamino]-1-phenyl-methylidene}-5-(3-aminophenylsulphonylamino)-2-indolinone | 217–218 |
| | D | 2-aminophenyl | H | pyrrolidin-1-ylmethyl | (Z)-3-{1-[4-(pyrrolidin-1-ylmethyl)-phenylamino)-1-phenyl-methylidene}-5-(2-aminophenylsulphonylamino)-2-indolinone | 260 |
| | Ex. 1 | methyl | H | acetylamino | (Z)-3-{1-[4-acetylamino-phenylamino)-1-phenyl-methylidene}-5-methylsulphonylamino-2-indolinone | 299–303 |
| | Ex. 1 | ethyl | H | 2-dimethylamino-acetylamino | (Z)-3-{1-[4-(2-dimethylamino-acetylamino)-phenylamino]-1-phenyl-methylidene}-5-ethylsulphonylamino-2-indolinone | 238–241 |
| | Ex. 1 | methyl | H | dimethylaminomethyl | (Z)-3-{1-[4-dimethylaminomethyl-phenylamino]-1-phenyl-methylidene}-5-methylsulphonylamino-2-indolinone | 240–242 |
| | Ex. 1 | n-propyl | H | dimethylaminomethyl | (Z)-3-{1-[4-dimethylaminomethyl-phenylamino]-1-phenyl-methylidene}-5-n-propylsulphonylamino-2-indolinone | 221–223 |
| | Ex. 1 | n-butyl | H | dimethylaminomethyl | (Z)-3-{1-[4-dimethylaminomethyl-phenylamino]-1-phenyl-methylidene}-5-n-butylsulphonylamino-2-indolinone | 210–213 |
| | Ex. 1 | ethyl | H | diethylaminomethyl | (Z)-3-{1-[4-diethylaminomethyl-phenylamino]-1-phenyl-methylidene}-5-ethylsulphonylamino-2-indolinone | 182–185 |
| | Ex. 1 | ethyl | H | N-(2-dimethyl-aminoethyl)-N-methylamino-carbonyl | (Z)-3-{1-[4-(N-(2-dimethylaminoethyl)-N-methylaminocarbonyl)-phenylamino]-1-phenyl-methylidene}-5-ethylsulphonylamino-2-indolinone | 201–203 |
| | Ex. 210 | ethyl | CH₃ | dimethylaminomethyl | (Z)-3-[1-(4-dimethylaminomethyl-phenylamino)-1-phenyl-methylidene]-5-(N-ethyl-N-phenylsulphonyl-amino)-2-indolinone | |
| | Ex. 1 | pyrid-2-yl | H | (S)-2-hydroxymethyl-pyrrolidin-1-ylmethyl | (Z)-3-{1-[4-((S)-2-hydroxymethylpyrrolid-1-ylmethyl)-phenylamino]-1-phenyl-methylidene}-5-pyrid-2-ylsulphonylamino-2-indolinone | sintering from 100 |
| | Ex. 1 | pyrid-2-yl | H | (S)-3-hydroxy-pyrrolidin-1-ylmethyl | (Z)-3-{1-[4-((S)-3-hydroxypyrrolid-1-ylmethyl)-phenylamino]-1-phenyl-methylidene}-5-pyrid-2-ylsulphonylamino-2-indolinone | sintering from 130 |

EXAMPLE 207

(Z)-3-{1-[4-(N-(2-dimethylamino-ethyl)-N-methyl-sulphonyl-amino)-phenylamino)-1-phenyl-methylidene}-5-(N-methyl-N-phenylsulphonyl-amino)-2-indolinone a. (Z)-1-acetyl-3-(1-ethoxy-1-phenyl-methylidene)-5-(N-methyl-N-phenylsulphonyl-amino)-2-indolinone 10 g (20 mmol) of 1-acetyl-3-(1-ethoxy-1-phenyl-methylidene)-5-(N-acetyl-N-phenylsulphonyl-amino)-2-indolinone (Example 1e) are dissolved in 150 ml of DMSO and combined with 2.2 g (20 mmol) of potassium tert. butoxide with stirring. After 15 minutes' stirring 1.9 ml (31 mmol) of iodomethane are added. The mixture is stirred for 3 hours at ambient temperature. Then another 2.2 g (20 mmol) of potassium tert. butoxide and 1 ml (16 mmol) of iodomethane are added. The mixture is stirred for 18 hours at ambient temperature. Then water is added. The reaction mixture is extracted with ethyl acetate. The organic phase is washed with water, dried over magnesium sulphate and evaporated to dryness. The residue is chromatographed on silica gel (petroleum ether/dichloromethane, 7:3).

Yield: 2.7 g (28% of theory) $R_f$ value: 0.65 (silica gel; dichloromethane/petroleum ether=8:2) $C_{26}H_{24}N_2O_5S$ (476.56) Mass spectrum: $(M+Na)^+=499$ b. (Z)-3-{1-[4-(N-(2-dimethylamino-ethyl)-N-methylsulphonyl-amino)-phenylamino)-1-phenyl-methylidene}-5-(N-methyl-N-phenylsulphonyl-amino)-2-indolinone Prepared analogously to Example 1f from 350 mg (0.73 mmol) of (Z)-1-acetyl-3-(1-ethoxy-1-phenyl-methylidene)-5-(N-methyl-N-phenylsulphonyl-amino)-2-indolinone and 257 mg (1 mmol) of 4-[N-(2-dimethylamino-ethyl)-N-methylsulphonyl-amino]-aniline in DMF and subsequent treatment with sodium hydroxide solution.

Yield: 380 mg (80% of theory) $R_f$ value: 0.5 (silica gel; dichloromethane/methanol/NH$_4$OH=9:1:0.1) $C_{33}H_{35}N_5O_5S_2$ (645.80) Mass spectrum: $M^+=645$

| Calc.: | C 61.38 | H 5.46 | N 10.84 |
|---|---|---|---|
| Found: | C 61.09 | H 5.45 | N 10.82 |

The following compounds of Examples 208 to 210 are prepared analogously to Example 207 using the intermediate products prepared in Examples I to XIII:

EXAMPLE 208

(Z)-3-{1-[4-(N-(2-dimethylamino-ethyl)-N-acetyl-amino)-phenylamino)-1-phenyl-methylidene}-5-(N-methyl-N-phenylsulphonyl-amino)-2-indolinone Melting point: 217° C. $R_f$ value: 0.5 (silica gel; dichloromethane/methanol/NH$_4$OH=9:1:0.1) $C_{34}H_{35}N_5O_4S$ (609.75) Mass spectrum: $(M+H)^+=610$

| Calc.: | C 66.97 | H 5.79 | N 11.49 |
|---|---|---|---|
| Found: | C 66.92 | H 5.78 | N 11.39 |

EXAMPLE 209

(Z)-3-{1-[4-(N-methyl-N-piperidinomethylcarbonyl-amino)-phenylamino)-1-phenyl-methylidene}-5-(N-methyl-N-phenylsulphonyl-amino)-2-indolinone Melting point: 160° C. $R_f$ value: 0.65 (silica gel; dichloromethane/methanol/NH$_4$OH=9:1:0.1) $C_{36}H_{37}N_5O_4S$ (635.79) Mass spectrum: $(M+H)^+=636$

EXAMPLE 210

(Z)-3-[1-(3-dimethylaminomethyl-phenylamino)-1-phenyl-methylidene]-5-(N-methyl-N-phenylsulphonyl-amino)-2-indolinone Melting point: 226° C. $R_f$ value: 0.75 (silica gel; dichloromethane/methanol/NH$_4$OH=9:1:0.1) $C_{31}H_{30}N_4O_3S$ (538.67) Mass spectrum: $(M+H)^+=539$ The following compounds may be obtained analogously to the foregoing Examples:

(1) (Z)-3-[1-(3-dimethylaminomethyl-phenylamino)-1-phenyl-methylidene]-5-ethylsulphonylamino-2-indolinone, melting point 222–224° C.

(2) (Z)-3-{1-[4-(2-dimethylaminoethyl)-phenylamino]-1-phenyl-methylidene}-5-methylsulphonylamino-2-indolinone (3) (Z)-3-[1-(4-diethylaminomethyl-phenylamino)-1-phenyl-methylidene]-5-methylsulphonylamino-2-indolinone (4) (Z)-3-[1-(4-dipropylaminomethyl-phenylamino)-1-phenyl-methylidene]-5-methylsulphonylamino-2-indolinone (5) (Z)-3-[1-(4-hexamethyleneiminomethyl-phenylamino)-1-phenyl-methylidene]-5-methylsulphonylamino-2-indolinone (6) (Z)-3-{1-[4-(4-methylpiperidinomethyl)-phenylamino]-1-phenyl-methylidene}-5-methylsulphonylamino-2-indolinone (7) (Z)-3-[1-(4-morpholinomethyl-phenylamino)-1-phenyl-methylidene]-5-methylsulphonylamino-2-indolinone (8) (Z)-3-{1-[4-(4-methylpiperazinomethyl)-phenylamino]-1-phenyl-methylidene}-5-methylsulphonylamino-2-indolinone (9) (Z)-3-[1-(4-piperazinomethyl-phenylamino)-1-phenyl-methylidene]-5-methylsulphonylamino-2-indolinone

(10) (Z)-3-{1-[4-(2,6-dimethylpiperidinomethyl)-phenylamino]-1-phenyl-methylidene}-5-methylsulphonylamino-2-indolinone

(11) (Z)-3-[1-(4-dipropylaminomethyl-phenylamino)-1-phenyl-methylidene]-5-ethylsulphonylamino-2-indolinone

(12) (Z)-3-[1-(4-hexamethyleneiminomethyl-phenylamino)-1-phenyl-methylidene]-5-ethylsulphonylamino-2-indolinone

(13) (Z)-3-{1-[4-(4-methylpiperidinomethyl)-phenylamino]-1-phenyl-methylidene}-5-ethylsulphonylamino-2-indolinone

(14) (Z)-3-[1-(4-morpholinomethyl-phenylamino)-1-phenyl-methylidene]-5-ethylsulphonylamino-2-indolinone

(15) (Z)-3-{1-[4-(4-methylpiperazinomethyl)-phenylamino]-1-phenyl-methylidene}-5-ethylsulphonylamino-2-indolinone

(16) (Z)-3-[1-(4-piperazinomethyl-phenylamino)-1-phenyl-methylidene]-5-ethylsulphonylamino-2-indolinone

(17) (Z)-3-{1-[4-(2,6-dimethylpiperidinomethyl)-phenylamino]-1-phenyl-methylidene}-5-ethylsulphonylamino-2-indolinone

(18) (Z)-3-[1-(4-piperazinomethyl-phenylamino)-1-phenyl-methylidene]-5-propylsulphonylamino-2-indolinone
(19) (Z)-3-{1-[4-(2,6-dimethylpiperidinomethyl)-phenylamino]-1-phenyl-methylidene}-5-propylsulphonylamino-2-indolinone
(20) (Z)-3-[1-(4-diethylaminomethyl-phenylamino)-1-phenyl-methylidene]-5-propylsulphonylamino-2-indolinone
(21) (Z)-3-[1-(4-dipropylaminomethyl-phenylamino)-1-phenyl-methylidene]-5-propylsulphonylamino-2-indolinone
(22) (Z)-3-[1-(4-hexamethyleneiminomethyl-phenylamino)-1-phenyl-methylidene]-5-propylsulphonylamino-2-indolinone
(23) (Z)-3-{1-[4-(4-methylpiperidinomethyl)-phenylamino]-1-phenyl-methylidene}-5-propylsulphonylamino-2-indolinone
(24) (Z)-3-[1-(4-morpholinomethyl-phenylamino)-1-phenyl-methylidene]-5-propylsulphonylamino-2-indolinone
(25) (Z)-3-{1-[4-(4-methylpiperazinomethyl)-phenylamino]-1-phenyl-methylidene}-5-propylsulphonylamino-2-indolinone
(26) (Z)-3-[1-(4-piperazinomethyl-phenylamino)-1-phenyl-methylidene]-5-cyclopropylsulphonylamio-2-indolinone
(27) (Z)-3-{1-[4-(2,6-dimethylpiperidinomethyl)-phenylamino]-1-phenyl-methylidene}-5-cyclopropylsulphonylamino-2-indolinone
(28) (Z)-3-[1-(4-dimethylaminomethyl-phenylamino)-1-phenyl-methylidene]-5-cyclopropylsulphonylamino-2-indolinone
(29) (Z)-3-{1-[4-(2-dimethylaminoethyl)-phenylamino]-1-phenyl-methylidene}-5-cyclopropylsulphonylamino-2-indolinone
(30) (Z)-3-[1-(4-diethylaminomethyl-phenylamino)-1-phenyl-methylidene]-5-cyclopropylsulphonylamino-2-indolinone
(31) (Z)-3-[1-(4-dipropylaminomethyl-phenylamino)-1-phenyl-methylidene]-5-cyclopropylsulphonylamino-2-indolinone
(32) (Z)-3-[1-(4-hexamethyleneiminomethyl-phenylamino)-1-phenyl-methylidene]-5-cyclopropylsulphonylamino-2-indolinone
(33) (Z)-3-{1-[4-(4-methylpiperidinomethyl)-phenylamino]-1-phenyl-methylidene}-5-cyclopropylsulphonylamino-2-indolinone
(34) (Z)-3-[1-(4-morpholinomethyl-phenylamino)-1-phenyl-methylidene]-5-cyclopropylsulphonylamino-2-indolinone
(35) (Z)-3-{1-[4-(4-methylpiperazinomethyl)-phenylamino]-1-phenyl-methylidene}-5-cyclopropylsulphonylamino-2-indolinone
(36) (Z)-3-[1-(4-piperazinomethyl-phenylamino)-1-phenyl-methylidene]-5-trifluoromethylsulphonylamino-2-indolinone
(37) (Z)-3-{1-[4-(2,6-dimethylpiperidinomethyl)-phenylamino]-1-phenyl-methylidene}-5-trifluoromethylsulphonylamino-2-indolinone
(38) (Z)-3-[1-(4-dimethylaminomethyl-phenylamino)-1-phenyl-methylidene]-5-trifluoromethylsulphonylamino-2-indolinone
(39) (Z)-3-{1-[4-(2-dimethylaminoethyl)-phenylamino]-1-phenyl-methylidene}-5-trifluoromethylsulphonylamino-2-indolinone
(40) (Z)-3-[1-(4-diethylaminomethyl-phenylamino)-1-phenyl-methylidene]-5-trifluoromethylsulphonylamino-2-indolinone
(41) (Z)-3-[1-(4-dipropylaminomethyl-phenylamino)-1-phenyl-methylidene]-5-trifluoromethylsulphonylamino-2-indolinone
(42) (Z)-3-{1-[4-(pyrrolidin-1-yl)-methyl-phenylamino]-1-phenyl-methylidene}-5-trifluoromethylsulphonylamino-2-indolinone
(43) (Z)-3-[1-(4-piperidinomethyl-phenylamino)-1-phenyl-methylidene]-5-trifluoromethylsulphonylamino-2-indolinone
(44) (Z)-3-[1-(4-hexamethyleneiminomethyl-phenylamino)-1-phenyl-methylidene]-5-trifluoromethylsulphonylamino-2-indolinone
(45) (Z)-3-{1-[4-(4-methylpiperidinomethyl)-phenylamino]-1-phenyl-methylidene}-5-trifluoromethylsulphonylamino-2-indolinone
(46) (Z)-3-[1-(4-morpholinomethyl-phenylamino)-1-phenyl-methylidene]-5-trifluoromethylsulphonylamino-2-indolinone
(47) (Z)-3-{1-[4-(4-methylpiperazinomethyl)-phenylamino]-1-phenyl-methylidene}-5-trifluoromethylsulphonylamino-2-indolinone
(48) (Z)-3-[1-(4-piperazinomethyl-phenylamino)-1-phenyl-methylidene]-5-isopropylsulphonylamino-2-indolinone
(49) (Z)-3-{1-[4-(2,6-dimethylpiperidinomethyl)-phenylamino]-1-phenyl-methylidene}-5-isopropylsulphonylamino-2-indolinone
(50) (Z)-3-[1-(4-dimethylaminomethyl-phenylamino)-1-phenyl-methylidene]-5-isopropylsulphonylamino-2-indolinone
(51) (Z)-3-[1-(4-diethylaminomethyl-phenylamino)-1-phenyl-methylidene]-5-isopropylsulphonylamino-2-indolinone
(52) (Z)-3-[1-(4-dipropylaminomethyl-phenylamino)-1-phenyl-methylidene]-5-isopropylsulphonylamino-2-indolinone
(53) (Z)-3-{1-[4-(pyrrolidin-1-yl)-methyl-phenylamino]-1-phenyl-methylidene}-5-isopropylsulphonylamino-2-indolinone
(54) (Z)-3-[1-(4-hexamethyleneiminomethyl-phenylamino)-1-phenyl-methylidene]-5-isopropylsulphonylamino-2-indolinone
(55) (Z)-3-{1-[4-(4-methylpiperidinomethyl)-phenylamino]-1-phenyl-methylidene}-5-isopropylsulphonylamino-2-indolinone
(56) (Z)-3-[1-(4-morpholinomethyl-phenylamino)-1-phenyl-methylidene]-5-isopropylsulphonylamino-2-indolinone
(57) (Z)-3-{1-[4-(4-methylpiperazinomethyl)-phenylamino]-1-phenyl-methylidene}-5-isopropylsulphonylamino-2-indolinone

EXAMPLE 211

Dry ampoule containing 75 mg of active substance per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 212

Dry ampoule containing 35 mg of active substance per 2 ml

Composition:

| Active substance | 35.0 mg |
|---|---|
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 213

Tablet containing 50 mg of active substance

Composition:

| (1) Active substance | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

EXAMPLE 214

Tablet containing 350 mg of active substance

Preparation:

| (1) Active substance | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

EXAMPLE 215

Capsules containing 50 mg of active substance

Composition:

| (1) Active substance | 50.0 mg |
|---|---|
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE 216

Capsules containing 350 mg of active substance

Composition:

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE 217

Suppositories containing 100 mg of active substance

| 1 suppository contains: | |
|---|---|
| active substance | 100.0 mg |
| polyethyleneglycol (M.W. 1500) | 600.0 mg |
| polyethyleneglycol (M.W. 6000) | 460.0 mg |
| polyethylenesorbitan monostearate | 840.0 mg |
| | 2,000.0 mg |

Preparation:

The polyethyleneglycol is melted together with polyethylene sorbitan monostearate. At 40° C. the ground active substance is homogeneously dispersed in the melt. It is cooled to 38° C. and poured into slightly chilled suppository moulds.

What is claimed is:

1. A compound of the formula I

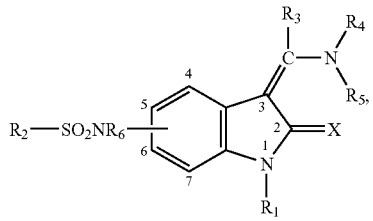

or a pharmaceutically acceptable salt thereof, wherein:
X is an oxygen or sulphur atom,
$R_1$ is a hydrogen atom, a $C_{1-4}$-alkoxycarbonyl or $C_{2-4}$-alkanoyl group,
$R_2$ is a $C_{1-6}$-alkyl group optionally substituted by one or more halogen atoms or a phenyl group or a $C_{2-6}$-alkenyl group optionally substituted by a phenyl group, wherein the phenyl moiety may be substituted in each case by a fluorine, chlorine, bromine or iodine atom, by a $C_{1-3}$-alkyl or $C_{1-3}$-alkoxy group,
a phenyl group which may be mono- or disubstituted by fluorine, chlorine, bromine or iodine atoms, by $C_{1-3}$-alkyl or $C_{1-3}$-alkoxy groups, wherein the substituents may be identical or different,
a phenyl group substituted by a trifluoromethyl, carboxy, $C_{1-3}$-alkoxycarbonyl, aminocarbonyl, cyano, aminomethyl, nitro or amino group,
a $C_{4-6}$-alkyl, $C_{3-7}$-cycloalkyl, trimethylphenyl or naphthyl group,
$R_3$ is a hydrogen atom or a $C_{1-6}$-alkyl group,
a phenyl group optionally substituted by a fluorine, chlorine or bromine atom, by a $C_{1-3}$-alkyl, hydroxy, $C_{1-3}$-alkoxy, $C_{1-3}$-alkylsulphenyl, $C_{1-3}$-alkylsulphinyl, $C_{1-3}$-alkylsulphonyl, phenylsulphenyl, phenylsulphinyl, phenylsulphonyl, nitro, amino, $C_{1-3}$-alkylamino, di-($C_{1-3}$-alkyl)-amino, $C_{2-5}$-alkanoylamino or N—($C_{1-3}$-alkylamino)-$C_{2-5}$-alkanoylamino group,
R4 is a phenyl or naphthyl group substituted by $R_7$, which may additionally be substituted by a chlorine or bromine atom or a nitro group,
$R_5$ and $R_6$ in each case independently of one another are hydrogen atoms or $C_{1-3}$-alkyl groups, and
$R_7$ is a $C_{1-3}$-alkyl group which is substituted by a piperidino group, while the abovementioned piperidino group may be substituted by one or two $C_{1-3}$-alkyl groups, which may in turn be terminally substituted by a hydroxy, amino or $C_{2-4}$-alkanoylamino group, or by a $C_{5-7}$-cycloalkyl or phenyl group and by a hydroxy group and in the abovementioned piperidino group a methylene group adjacent to the nitrogen atom may be replaced by a carbonyl group.

2. A compound of formula I according to claim 1 wherein the sulphonylamino group of the formula $R_2$—$SO_2NR_6$— is linked to the 5-position of the indolinone group.

3. A compound of formula I according to claim 1, wherein:
$R_3$ is a phenyl group optionally substituted by a fluorine, chlorine or bromine atom, by a $C_{1-3}$-alkyl, hydroxy, $C_{1-3}$-alkoxy, $C_{1-3}$-alkylsulphenyl, $C_{1-3}$-alkylsulphinyl, $C_{1-3}$-alkylsulphonyl, phenylsulphenyl, phenylsulphinyl, phenylsulphonyl, nitro, amino, $C_{1-3}$-alkylamino, di-($C_{1-3}$-alkyl)-amino, $C_{2-5}$-alkanoylamino or N—($C_{1-3}$-alkylamino)-$C_{2-5}$-alkanoylamino group.

4. A compound of formula I according to claim 1, wherein:
$R_2$ is a $C_{1-3}$-alkyl group optionally substituted by one or more halogen atoms or a phenyl group or a $C_{2-4}$-alkenyl group optionally substituted by a phenyl group, wherein the phenyl moiety in each case may be substituted by a fluorine, chlorine, bromine or iodine atom or by a $C_{1-3}$-alkyl or $C_{1-3}$-alkoxy group.

5. A compound of formula I according to claim 1, wherein:
X is an oxygen atom,
$R_1$ is a hydrogen atom,
$R_2$ is a $C_{1-3}$-alkyl group optionally substituted by one or more fluorine atoms or a phenyl group or a $C_{2-4}$-alkenyl group optionally substituted by a phenyl group;
a phenyl group which may be mono- or disubstituted by fluorine, chlorine, bromine or iodine atoms, by $C_{1-3}$-alkyl or $C_{1-3}$-alkoxy groups, wherein the substituents may be identical or different,
a phenyl group substituted by a trifluoromethyl, carboxy, $C_{1-3}$-alkoxycarbonyl, aminocarbonyl, cyano, aminomethyl, nitro or amino group, or
a $C_{4-6}$-alkyl, $C_{3-7}$-cycloalkyl, trimethylphenyl or naphthyl group,
$R_3$ is a hydrogen atom or a $C_{1-4}$-alkyl group, or
a phenyl group optionally substituted by a fluorine, chlorine, bromine or iodine atom, by a $C_{1-3}$-alkyl, $C_{1-3}$-alkoxy, nitro or amino group,
$R_4$ is a phenyl group substituted by $R_7$,
$R_5$ and $R_6$ in each case denote a hydrogen atom, and
$R_7$ is a $C_{1-3}$-alkyl group which is substituted by a piperidino group,
while abovementioned piperidino group may be substituted by one or two $C_{1-3}$-alkyl groups, which may in turn be terminally substituted by a hydroxy, amino or $C_{2-4}$-alkanoylamino group, and at the same time in the abovementioned piperidino group a methylene group in the 2 position may be replaced by a carbonyl group.

6. A compound of formula I according to claim 1, wherein:
$R_2$ is a $C_{1-3}$-alkyl group optionally substituted by a phenyl group, a $C_{1-3}$-perfluoroalkyl group or a phenylvinyl group, or
a phenyl group which may be substituted by a fluorine, chlorine, bromine or iodine atom, by
a $C_{1-3}$-alkyl, $C_{1-3}$-alkoxy, nitro, amino, cyano, or aminomethyl group,
a $C_{4-6}$-alkyl, $C_{3-7}$-cycloalkyl, trimethylphenyl or naphthyl group,
$R_3$ is a phenyl group optionally substituted by a fluorine, chlorine, bromine or iodine atom, by a $C_{1-3}$-alkyl, $C_{1-3}$-alkoxy, nitro or amino group,
$R_4$ is a phenyl group which is substituted by $R_7$ and additionally by a chlorine atom or a nitro group, while
$R_7$ is a methyl or ethyl group which is substituted by a piperidino group.

7. A compound of formula I according to claim 1, wherein $R_4$ is a phenyl group substituted in the 4 position by $R_7$.

8. A compound of the formula IA

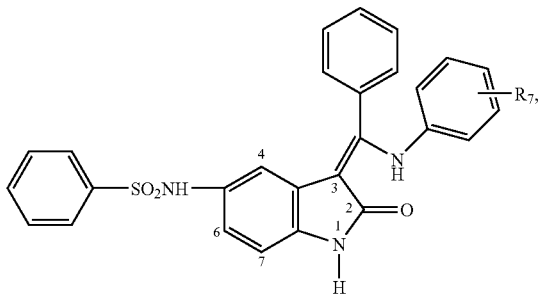

(IA)

wherein $R_7$ is defined as in claim 1, 5 or 6.

9. A compound of formula IA according to claim 8 wherein $R_7$ is selected from the group consisting of: (2,6-dimethylpiperidino)-methyl, and 2-oxopiperidinomethyl.

10. A compound of formula IB

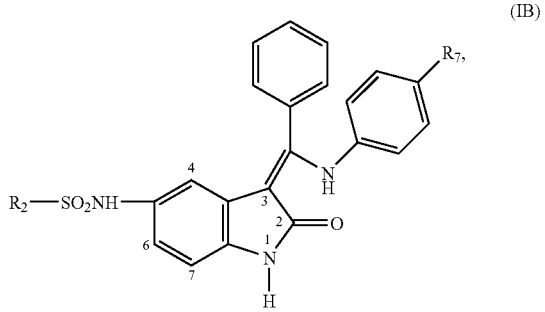

(IB)

wherein $R_2$ and $R_7$ are defined as in claim 1, 4, 5 or 6.

11. A compound of formula IB according to claim 10 wherein:

$R_7$ is selected from the group consisting of: (2,6-dimethylpiperidino)-methyl and $R_2$ is selected from the group consisting of: 2-aminophenyl, 2-chlorophenyl, 2-cyanophenyl, 2-nitrophenyl, 2-phenylethene, 3-aminomethylphenyl, 3-aminophenyl, 3-chlorophenyl, 3-cyanophenyl, 3-methoxyphenyl, 3-methylphenyl, 3-nitrophenyl, 4-aminophenyl, 4-chlorophenyl, 4-methoxyphenyl, 4-methylphenyl, 4-nitrophenyl, ethyl, isopropyl, methyl, propyl and 2,4,6-trimethylphenyl.

12. A compound selected from the group consisting of:
(Z)-3-{1-[4-((2,6-dimethylpiperidino)-methyl)-phenylamino]-1-phenyl-methylidene}-5-(3-nitrophenylsulphonylamino)-2-indolinone,
(Z)-3-[1-(4-piperidinomethyl-phenylamino)-1-phenyl-methylidene]-5-methylsulphonylamino-2-indolinone,
(Z)-3-{1-[4-(piperidinomethyl)-phenylamino]-1-phenyl-methylidene}-5-ethylsulphonylamino-2-indolinone,
(Z)-3-{1-[4-(piperidinomethyl)-phenylamino]-1-phenyl-methylidene}-5-isopropylsulphonylamino-2-indolinone,
(Z)-3-{1-[4-(piperidinomethyl)-phenylamino]-1-phenyl-methylidene}-5-(3-nitrophenylsulphonylamino)-2-indolinone, and
(Z)-3-[1-(4-piperidinomethyl-phenylamino)-1-phenyl-methylidene]-5-(4-aminophenylsulphonylamino)-2-indolinone,
or a pharmaceutically acceptable salt thereof.

13. A pharmaceutical preparation comprising a compound according to claim 1, 2, 3, 4, 5, 6, 7, or 12 and a pharmaceutically acceptable carrier.

* * * * *